US009747572B2

(12) United States Patent
Watanabe

(10) Patent No.: US 9,747,572 B2
(45) Date of Patent: Aug. 29, 2017

(54) EXERCISE SUPPORT DEVICE, EXERCISE SUPPORT METHOD, AND EXERCISE SUPPORT PROGRAM

(71) Applicant: CASIO COMPUTER CO., LTD., Shibuya-ku, Tokyo (JP)

(72) Inventor: Kohei Watanabe, Fussa (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 653 days.

(21) Appl. No.: 14/221,278

(22) Filed: Mar. 20, 2014

(65) Prior Publication Data
US 2014/0288681 A1    Sep. 25, 2014

(30) Foreign Application Priority Data
Mar. 21, 2013    (JP) .................................. 2013-057667

(51) Int. Cl.
| | |
|---|---|
| *A61B 5/00* | (2006.01) |
| *G06Q 10/06* | (2012.01) |
| *A61B 5/107* | (2006.01) |
| *A61B 5/11* | (2006.01) |
| *G01P 13/00* | (2006.01) |

(52) U.S. Cl.
CPC ....... *G06Q 10/0639* (2013.01); *A61B 5/1071* (2013.01); *A61B 5/1122* (2013.01); *A61B 5/6824* (2013.01); *A61B 5/6828* (2013.01); *A61B 5/6898* (2013.01); *G01P 13/00* (2013.01)

(58) Field of Classification Search
CPC .................................................. A63B 24/0062
See application file for complete search history.

(56) References Cited

U.S. PATENT DOCUMENTS 8,460,001 B1 *    6/2013    Chuang .............. G09B 19/0038
                                                     434/247

FOREIGN PATENT DOCUMENTS

| | | |
|---|---|---|
| JP | 07-289540 A | 11/1995 |
| JP | 10-290854 A | 11/1998 |

* cited by examiner

*Primary Examiner* — Reginald Renwick
(74) *Attorney, Agent, or Firm* — Holtz, Holtz & Volek PC

(57) ABSTRACT

An exercise support device of the present invention includes a detecting section which detects motion data related to a motion status of a user performing an exercise and an swing-angle obtaining section which obtains an swing angle of the user and an information notifying section which notifies the user of exercise support information for guiding the swing angle to a suitable angle. When the user is in a specific motion state with an swing motion of a part which is an arm or a leg of the user, the swing-angle obtaining section successively tracks a swing status in one cycle of the swing motion in the specific motion state based on the motion data detected by the detecting section, and obtains a maximum value of differences between angles of the part of the user at two different timings in the one cycle as the swing angle.

19 Claims, 12 Drawing Sheets

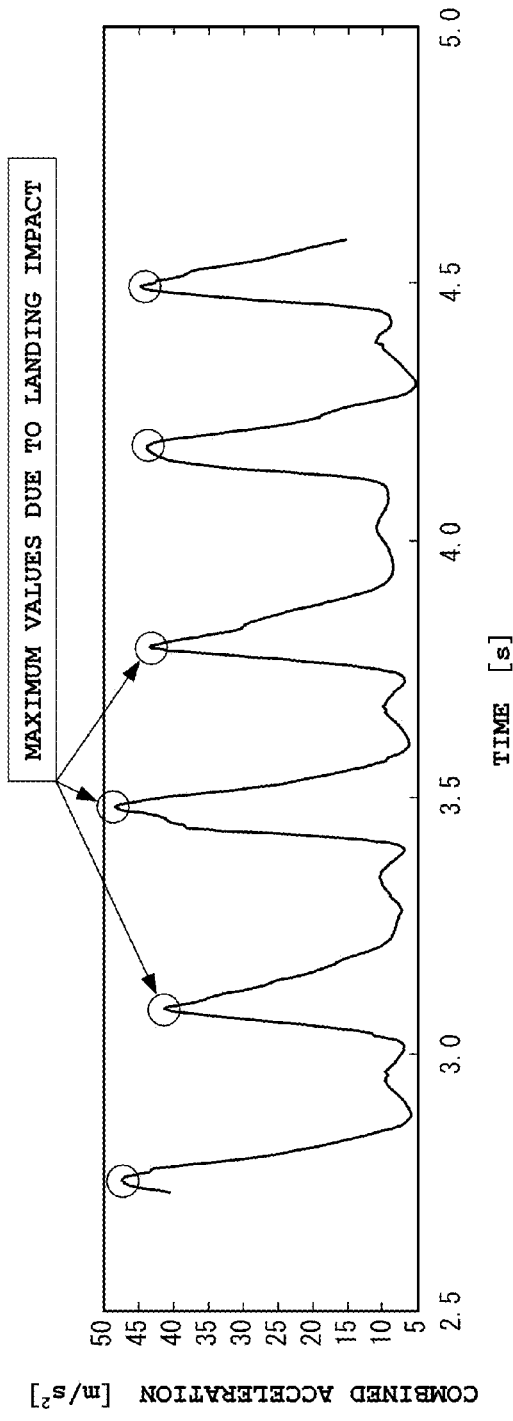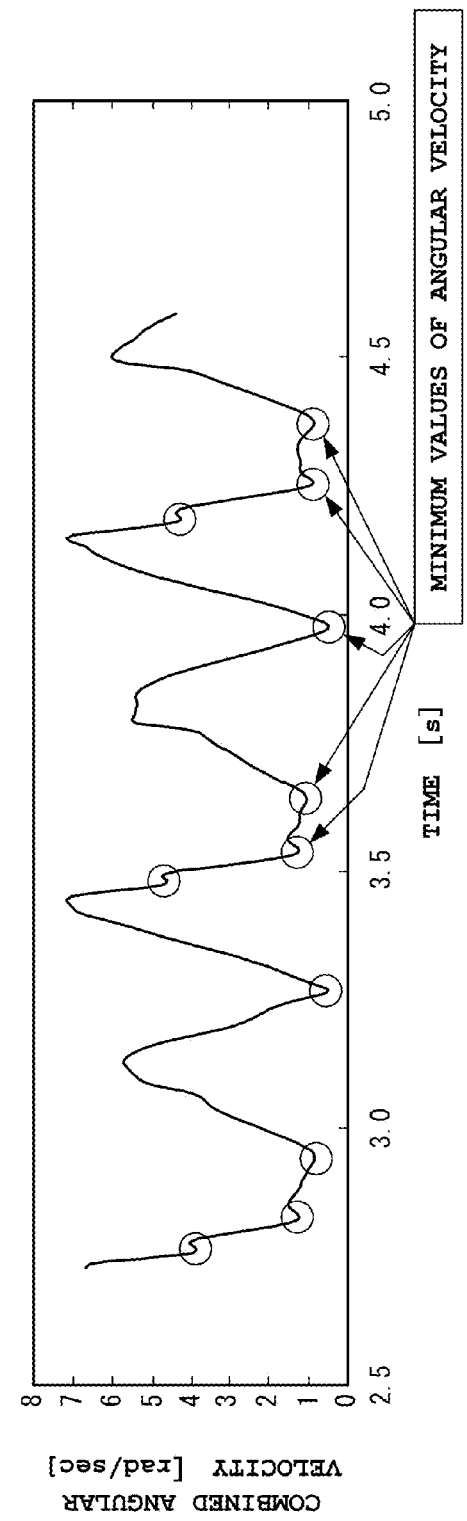

EXERCISE SUPPORT DEVICE, EXERCISE SUPPORT METHOD, AND EXERCISE SUPPORT PROGRAM

CROSS-REFERENCE TO RELATED APPLICATION

This application is based upon and claims the benefit of priority from the prior Japanese Patent Application No. 2013-057667, filed Mar. 21, 2013, the entire contents of which are incorporated herein by reference.

BACKGROUND OF THE INVENTION

1. Field of the Invention

The present invention relates to an exercise support device, an exercise support method, and an exercise support program. Specifically, the present invention relates to an exercise support device, an exercise support method, and an exercise support program by which the exercise status (exercise motion status) of a human body performing exercise is ascertained and guided to an appropriate state.

2. Description of the Related Art

In recent years, because of rising health consciousness, more and more people are performing daily exercises, such as running and walking, to maintain their wellness or improve their health condition. In addition, an increasing number of people are aiming to participate in various competitions and races through these daily exercises.

In order to achieve efficient and effective exercises, these people are very conscious of and interested in measuring and recording their own exercise motion status as numerical values and data and utilizing the numerical values and data for training.

Here, as a method for accurately ascertaining an exercise motion status, a method is known to be effective which uses various indexes, such as the pace and pitch of exercise, pulse rate, body temperature, blood pressure, respiratory rate, and energy consumption.

In Japanese Patent Application Laid-Open (Kokai) Publication No. 10-290854, a method for ascertaining an exercise motion status using these indexes is described.

In an exercise motion such as running or walking, the degree of arm swing among these various indexes, which represents how much arms are swinging during an exercise motion, is considered to be an important index for judging whether an exercising person is efficiently performing exercise (running or walking).

However, a technology capable of accurately ascertaining the degree of arm swing (whether arms are sufficiently swinging or not) and suitably transmitting information obtained by the ascertainment to the exercising person has not yet been established.

SUMMARY OF THE INVENTION

The present invention can advantageously provide an exercise support device, an exercise support method, and an exercise support program capable of accurately judging the degree of arm swing in an exercise motion, suitably transmitting the exercise motion status to the exercising person, and guiding the exercising person to an appropriate exercise motion status.

In accordance with one aspect of the present invention, there is provided an exercise support device comprising: a detecting section which detects motion data related to a motion status of a user performing an exercise, a swing-angle obtaining section which obtains a swing angle of a part which is an arm or a leg of the user when the user is in a specific motion state with a swing motion of the part; and an information notifying section which notifies the user of exercise support information for guiding the swing angle to a suitable angle based on the swing angle obtained by the swing-angle obtaining section, wherein the swing-angle obtaining section successively tracks an swing status in one cycle of the swing motion in the specific motion state based on the motion data detected by the detecting section, and obtains a maximum value of differences between angles of the part of the user at two different timings in the one cycle as the swing angle.

In accordance with another aspect of the present invention, there is provided an exercise support method comprising: a step of detecting motion data related to a motion status of a user performing an exercise, a step of, when the user is in a specific motion state with an swing motion of a part which is an arm or a leg of the user, successively tracking an swing status in one cycle of the swing motion in the specific motion state based on the motion data, and obtaining a maximum value of differences between angles of the part of the user at two different timings in the one cycle as an swing angle; and a step of notifying the user of exercise support information for guiding the swing angle to a suitable angle based on the swing angle.

In accordance with another aspect of the present invention, there is provided a non-transitory computer-readable storage medium having stored thereon an exercise support program that is executable by a computer, the program being executable by the computer to perform functions comprising: processing for detecting motion data related to a motion status of a user performing an exercise; and processing for, when the user is in a specific motion state with an swing motion of a part which is an arm or a leg of the user, successively tracking an swing status in one cycle of the swing motion in the specific motion state based on the motion data, and calculating a maximum value of differences between angles of the part of the user at two different timings in the one cycle as an swing angle; and processing for notifying the user of exercise support information for guiding the swing angle to a suitable angle based on the swing angle.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

BRIEF DESCRIPTION OF THE DRAWINGS

FIG. 5A and FIG. 5B are waveform diagrams each depicting an example of the signal waveform of sensor data obtained in the exercise support method according to the first embodiment.

DETAILED DESCRIPTION OF TEE PREFERRED EMBODIMENTS

An exercise support device, an exercise support method, and an exercise support program according to the present invention are described in detail below with reference to the drawings.

Note that, in the embodiments described below, a case is described in which a user performs a walking exercise (walking) or a running exercise (running).

Also note that, although a case in which an arm-swing angle is obtained is described in the embodiments described below, the present invention is not limited thereto, and a leg-swing angle may be obtained instead of this arm-swing angle.

First Embodiment (Exercise Support Device)

Figure 1A:
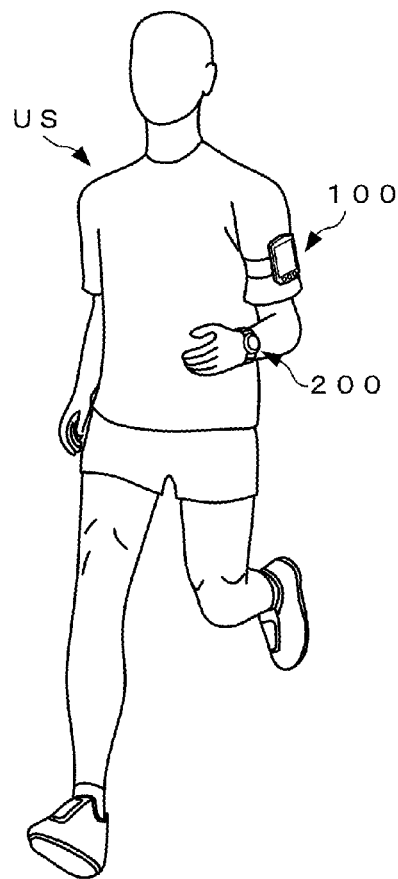
FIG. 1A, FIG. 1B and FIG. 1C are schematic structural diagrams each depicting an exercise support device according to a first embodiment of the present invention.
Figure 1B:
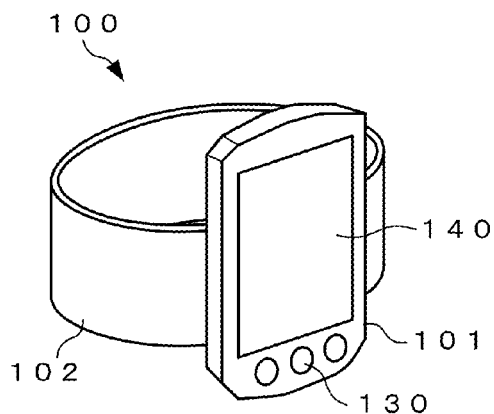
Figure 1C:
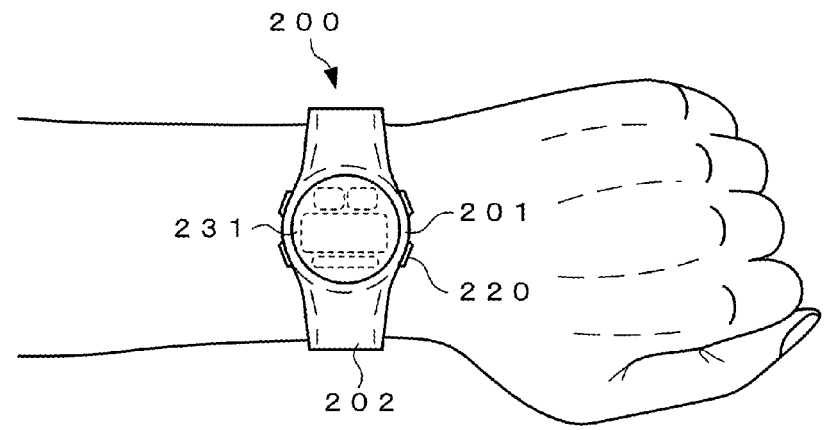

FIG. 1A, FIG. 1B and FIG. 1C are schematic structural diagrams each depicting an exercise support device of a first embodiment according to the present invention. FIG. 1A is a schematic diagram depicting a state in which the exercise support device according to the present embodiment has been worn on a human body. FIG. 1B is a schematic structural diagram depicting an example of a terminal of the exercise support device which is worn on an upper arm portion. FIG. 1C is a schematic structural diagram depicting an example of a state in which a terminal of the exercise support device for a forearm portion has been worn on a forearm portion.

Figure 2A:
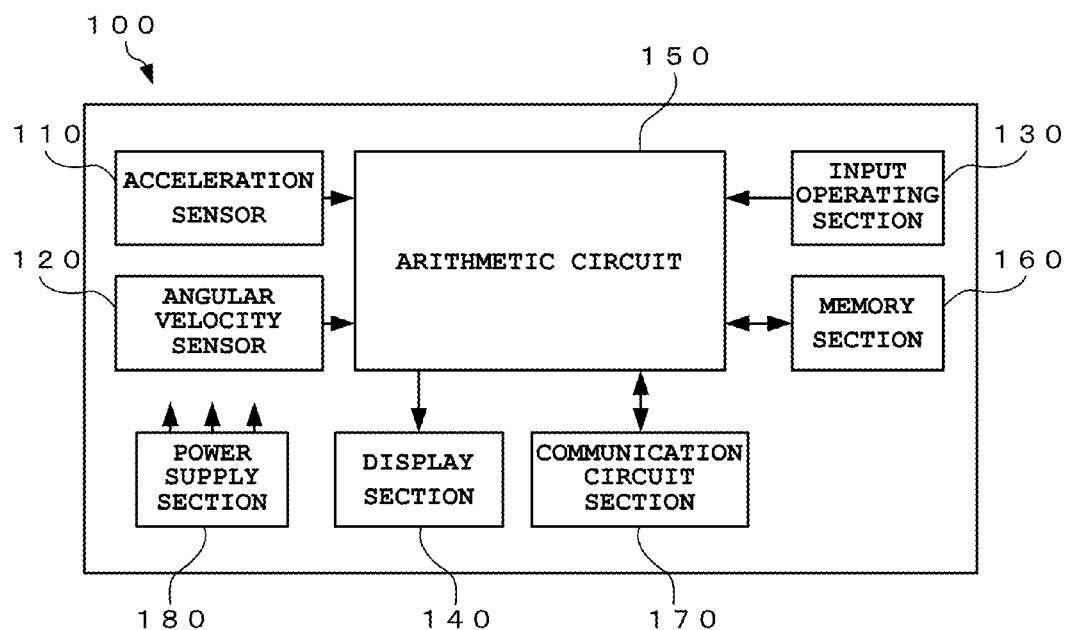
FIG. 2A and FIG. 2B are functional block diagrams each depicting a structural example of the exercise support device according to the first embodiment.
Figure 2B:
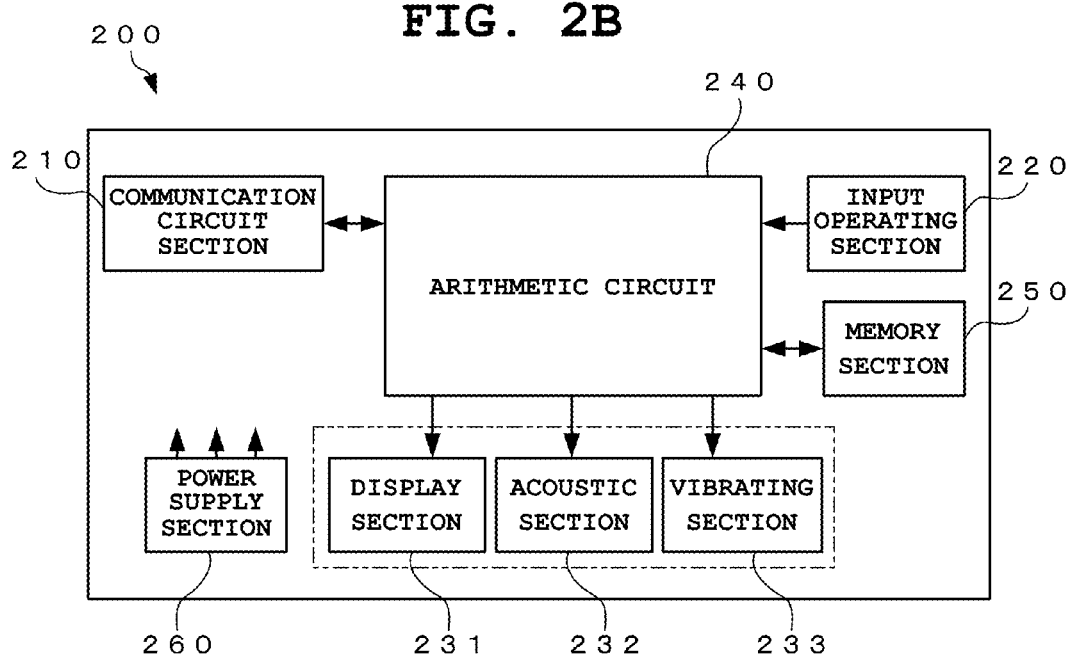

FIG. 2A and FIG. 2B are functional block diagrams each depicting a structural example of the exercise support device according to the present embodiment. FIG. 2A is a schematic structural view depicting a structural example of the terminal of the exercise support device which is worn on an upper arm portion, and FIG. 2B is a schematic structural view depicting a structural example of the terminal of the exercise support device which is worn on a forearm portion.

The exercise support device according to the present embodiment is structured to have, for example, a terminal (a first terminal) 100 that is worn on an upper arm portion of a user US who is performing exercise and a terminal (a second terminal) 200 that is worn on a forearm portion (wrist), as depicted in FIG. 1A to FIG. 1C.

(Terminal 100)

The terminal 100 has an outer appearance and shape of, for example, a forearm-worn type (or an armband type), as depicted in FIG. 1B.

The terminal 100 mainly includes a device body 101 which ascertains the exercise motion status of the user US and obtains exercise motion information indicating the exercise motion status, and a belt section 102 that is wound around an upper arm portion of the user US so that the device body 101 is worn thereon.

Specifically, the terminal 100 mainly includes, for example, an acceleration sensor (detecting section) 110, an angular velocity sensor (detecting section) 120, an input operating section 130, a display section 140, an arithmetic circuit (motion status judging section, arm-swing-angle obtaining section, arm-swing status judging section, and information notifying section) 150, a memory section (evaluation information storage section) 160, a communication circuit section 170, and a power supply section 180, as depicted in FIG. 2A.

The acceleration sensor 110 has, for example, a triaxial acceleration sensor.

This triaxial acceleration sensor detects accelerations in three axial (x axis, y axis, and z axis) directions orthogonal to one another exerted on the terminal 100 when the user US is performing exercise, and outputs a signal corresponding to the magnitude of the detected acceleration in each axial direction as acceleration data.

The acceleration data outputted from the acceleration sensor 110 has signal components corresponding to the respective three axial directions and associated with accelerations in a forward-backward direction, a leftward-rightward direction, an upward-downward direction of the body of the user US performing exercise.

These acceleration data corresponding to the three axial directions are combined at the arithmetic circuit 150, which will be described further below, and the combined data is associated with temporal data and stored in a predetermined storage area of the memory section 160.

The angular velocity sensor 120 has, for example, a triaxial angular velocity sensor.

This triaxial angular velocity sensor detects angular velocities in three axial (x axis, y axis, and z axis) directions orthogonal to one another exerted on the terminal 100 when the user US is performing exercise, and outputs a signal corresponding to the magnitude of the detected angular velocity in each axial direction as acceleration data.

The angular velocity data outputted from the angular velocity sensor 120 has signal components corresponding to the respective three axial directions and associated with angular velocities in a forward-backward direction, a leftward-rightward direction, an upward-downward direction of the arm of the user US performing exercise.

These angular velocity data in three axial directions are combined at the arithmetic circuit 150, which will be described further below, and the combined data is associated with temporal data and stored in a predetermined storage area of the memory section 160.

The input operating section 130 has input means such as an operation switch provided on the front surface or side surface of the device body 101, a touch panel provided on the front surface side (visual field side) of the display section 140 described below, and a keyboard connected to the device body 101 via wired or wireless communication, as depicted in FIG. 1B.

The input operating section 130 is used for various input operations such as the ON/OFF control of a sensing operation (measuring operation) in the acceleration sensor 110 and the angular velocity sensor 120, the input of evaluation of an arm-swing status described below, and the setting of various items displayed on the display section 140.

Note that, here, a configuration where only one of the operation switch, the touch panel, and the keyboard is provided may be adopted, and a configuration where various input means such as these are provided may also be adopted.

In the configuration where a plurality of input means are included, functions achieved by the respective input means may be identical or equivalent to each other, or each of the input means may have a unique function.

The display section 140 has a display panel of, for example, a liquid-crystal type capable of color or monochrome display or a light-emitting-element type such as an organic EL element.

The display section 140 displays exercise motion information generated based on sensor data obtained by the acceleration sensor 110 and the angular velocity sensor 120, time information such as present time and elapsed time for sensing operation, an input screen for evaluating an exercise motion status, a screen for setting a method for notifying of exercise support information, and the like.

These pieces of information have character information and image information, which may be singly or simultaneously displayed on the display section 140. Alternatively, they may be sequentially displayed by the input operating section 130 being operated.

In the case of a structure where the above-described various information, an input screen, a setting screen, and the like are displayed on a display section 231 of a terminal 200 described below or a display section of another electronic device connected to the terminal 100 via wired or wireless communication, the terminal 100 may have a structure where the display section 140 is not provided in the device body 101.

Another electronic device herein may be a dedicated device such as the terminal 200 or a general-purpose information communication device such as a personal computer, tablet terminal, or smartphone (high-functionality portable telephone).

The memory section 160 mainly has a data memory, a program memory, and a working memory.

The data memory has a non-volatile memory such as a flash memory. Sensor data obtained by the acceleration sensor 110 and the angular velocity sensor 120 is associated with temporal data and stored in a predetermined storage area.

Also, in an exercise support method described below, exercise motion information generated based on sensor data, evaluation information indicating whether or not an exercise motion status is desirable, exercise support information based on a judgment result of an exercise motion status, and the like are stored in a predetermined storage area of the data memory.

The program memory has a ROM (Read Only Memory). In the program memory, a control program for performing a predetermined operation in each section is stored. Examples of the predetermined operation include a sensing operation by the acceleration sensor 110 and the angular velocity sensor 120 and an operation of displaying various information by the display section 140.

Also, in the program memory, an algorithm program for performing a series of exercise support operations (exercise support method) is stored. In the series of exercise support operations, based on exercise motion information provided with evaluation information by the user US, a judgment is made whether or not the exercise motion status of the user US is desirable, and then the user US is guided to an appropriate exercise motion status.

The working memory has a RAM (Random Access Memory). In the working memory, various data to be used and various data generated when the control program and the algorithm program are executed are temporarily stored.

Note that the entire or part of the memory section 160 may be in a form of a removable storage medium such as a memory card, and may be structured to be removable from the terminal 100 (or the device body 101).

The arithmetic circuit 150 is an arithmetic operation device such as a CPU (Central Processing Unit) or an MPU (Microprocessor) having a clocking function.

The arithmetic circuit 150 executes a predetermined control program stored in the memory section 160 (program memory) based on a predetermined operation clock, and thereby controls various operations such as a sensing operation by the acceleration sensor 110 and the angular velocity sensor 120 and an information display operation by the display section 140.

Also, the arithmetic circuit 150 executes a predetermined algorithm program stored in the memory section 160 (program memory) based on the operation clock, and thereby executes the series of exercise support operations for ascertaining and judging the exercise motion status of the user US and guiding the user US to an appropriate exercise motion status.

The control program and the algorithm program to be executed in the arithmetic circuit 150 may be incorporated in advance in the arithmetic circuit 150.

The communication circuit section 170 functions as an interface when transmitting exercise motion information, the exercise support information, and the like generated based on sensor data obtained by the acceleration sensor 110 and the angular velocity sensor 120 to the terminal 200 described below.

Here, as a method for transmitting and receiving the exercise support information and the like between the terminal 100 and the terminal 200 via the communication circuit section 170, for example, various wireless communication methods and wired communication methods using a communication cable can be applied.

In the case where the exercise support information and the like are transmitted and received by using a wireless communication method, Bluetooth (registered trademark) which is a short-range wireless communication standard for digital devices, Bluetooth (registered trademark) low energy (LE) developed therein as a communication standard of a low-consumption power type, or a communication method equivalent thereto can be favorably applied.

By the wireless communication method, data transmission can be favorably performed even with low electric power generated by using an energy harvesting technology for the power supply section 180 described below.

The power supply section 180 supplies drive electric power to each section in the device body 101 of the terminal 100.

As the power supply section 180, for example, a primary battery such as a commercially-available coin-shaped battery or button-shaped battery or a secondary battery such as a lithium-ion battery or a nickel-metal-hydride battery can be applied.

Also, as the power supply section 180, a power supply by an energy harvest technology for generating electricity by energy such as vibrations, light, heat, and electro-magnetic waves can be applied in addition to the primary battery and the secondary battery.

(Terminal 200)

The terminal 200 has an outer appearance and shape of, for example, a forearm-worn type (or a wristwatch type), as depicted in FIG. 1C.

The terminal 200 mainly includes a device body 201 which notifies the user of exercise motion information obtained by the terminal 100 and the exercise support information based on exercise motion information and a belt section 202 that is wound around a forearm portion (wrist) of the user US so that the device body 201 is worn thereon.

Specifically, the terminal 200 mainly includes, for example, a communication circuit section 210, an input operating section 220, a display section (information notifying section) 231, an acoustic section (information notifying section) 232, a vibrating section (information notifying section) 233, an arithmetic circuit 240, a memory section 250, and a power supply section 260, as depicted in FIG. 2B.

The communication circuit section 210 functions as an interface when receiving, from the terminal 100, exercise motion information, the exercise support information, and the like obtained by the terminal 100.

Here, as a method for transmitting and receiving exercise motion information, the exercise support information, and the like to and from the terminal 100 via the communication circuit section 210, the various wireless communication methods and wired communication methods described above can be applied.

The input operating section 220 has input means such as an operation switch provided on the front surface or side surface of the device body 201, a touch panel provided on the front surface side (visual field side) of the display section 231 described below, and a keyboard connected to the device body 201 via wired or wireless communication, as depicted in FIG. 1C.

The input operating section 220 is used for input operations such as the ON/OFF control of the operation of notifying of the exercise support information based on a result of the judgment of an exercise motion status in the terminal 100 and the setting of various items displayed on the display section 140.

Note that, here, a configuration where only one of the operation switch, the touch panel, and the keyboard is provided may be adopted, and a configuration where various input means such as these are provided may also be adopted, as with the terminal 100.

The display section 231 has a display panel of, for example, a liquid-crystal type capable of color or monochrome display or a light-emitting-element type such as an organic EL element.

The display section 231 displays exercise motion information generated based on sensor data obtained by the terminal 100, time information such as present time and elapsed time for sensing operation, the exercise support information based on a judgment result of an exercise motion status, and the like.

These pieces of information have character information and image information, which may be singly or simultaneously displayed on the display section 231. Alternatively, they may be displayed sequentially.

The acoustic section 232 has an acoustic device that emits sound, such as a buzzer or a loudspeaker.

The acoustic section 232 generates sound information such as a predetermined timbre and sound pattern (alarm sound) and audio message, and thereby acoustically notifies the user US of the exercise support information according to a result of judgment regarding whether or not the exercise motion status of the user US is desirable in the exercise support method described below.

The vibrating section 233 has a vibrating device (a vibrator) that generates vibrations, such as a vibration motor or an oscillator.

This vibrating section 233 generates vibration information including a predetermined vibration pattern and its level, and thereby tactilely notifies the user US of the exercise support information according to a result of judgment regarding whether or not the exercise motion status of the user US is desirable in the exercise support method described below.

Note that the terminal 200 according to the present embodiment may include only the display section 231 as the information notifying means which notifies the user US of the exercise support information.

Alternatively, the terminal 200 may be structured to include one of the acoustic section 232 and the vibrating section 233 in addition to or in place of the display section 231.

As with the terminal 100, the memory section 250 mainly has a data memory, a program memory and a working memory.

In the data memory, the exercise support information and the like obtained by the terminal 100 and received via the communication circuit section 210 are stored in a predetermined storage area.

In the program memory, a control program for performing a predetermined operation in each section is stored. Examples of the predetermined operation include a data transmitting operation by the communication circuit section 210 and an operation of notifying the user of the exercise support information and the like by the display section 231, the acoustic section 232, and the vibrating section 233.

In the working memory, various data to be used and various data generated when the control program is executed are temporarily stored.

As with the terminal 100, the entire or part of the memory section 250 may be in a form as a removable storage medium, and may be structured to be removable from the terminal 200 (or the device body 201).

As with the terminal 100, the arithmetic circuit 240 is an arithmetic operation device such as a CPU or an MPU having a clocking function.

The arithmetic circuit 240 executes a predetermined control program stored in the memory section 250 based on a predetermined operation clock, and thereby controls various operations such as the data transmitting operation by the communication circuit section 210 and the operation of notifying the user of the exercise support information and the like by the display section 231, the acoustic section 232, and the vibrating section 233.

The control program to be executed in the arithmetic circuit 240 may be incorporated in advance in the arithmetic circuit 240.

The power supply section 260 supplies drive electric power to each section in the device body 201 of the terminal 200.

As with the power supply section 180 of the terminal 100, a primary battery or secondary battery can be applied as the power supply section 260, and a power supply by an energy harvesting technology or the like can also be applied.

(Exercise Support Method)

Next, an exercise support method in the exercise support device according to the present embodiment is described.

Here, an exercise support method for a case where the user US is performing a running exercise as an exercise motion is described.

Figure 3:
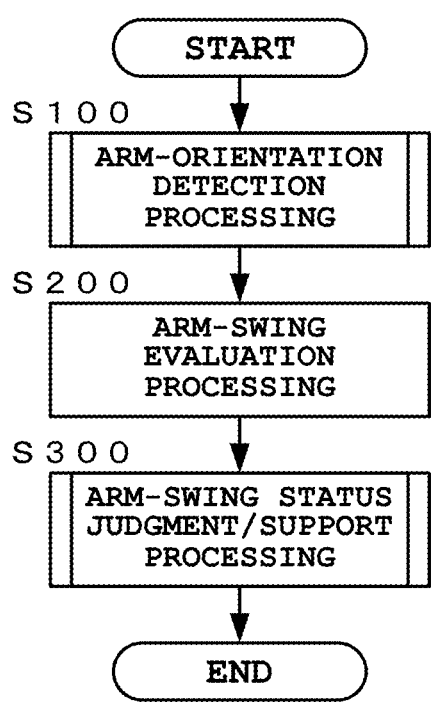
FIG. 3 is a flowchart depicting an example of an exercise support method in the exercise support device according to the first embodiment.

FIG. 3 is a flowchart depicting an example of the exercise support method in the exercise support device according to the present embodiment.

Figure 4:
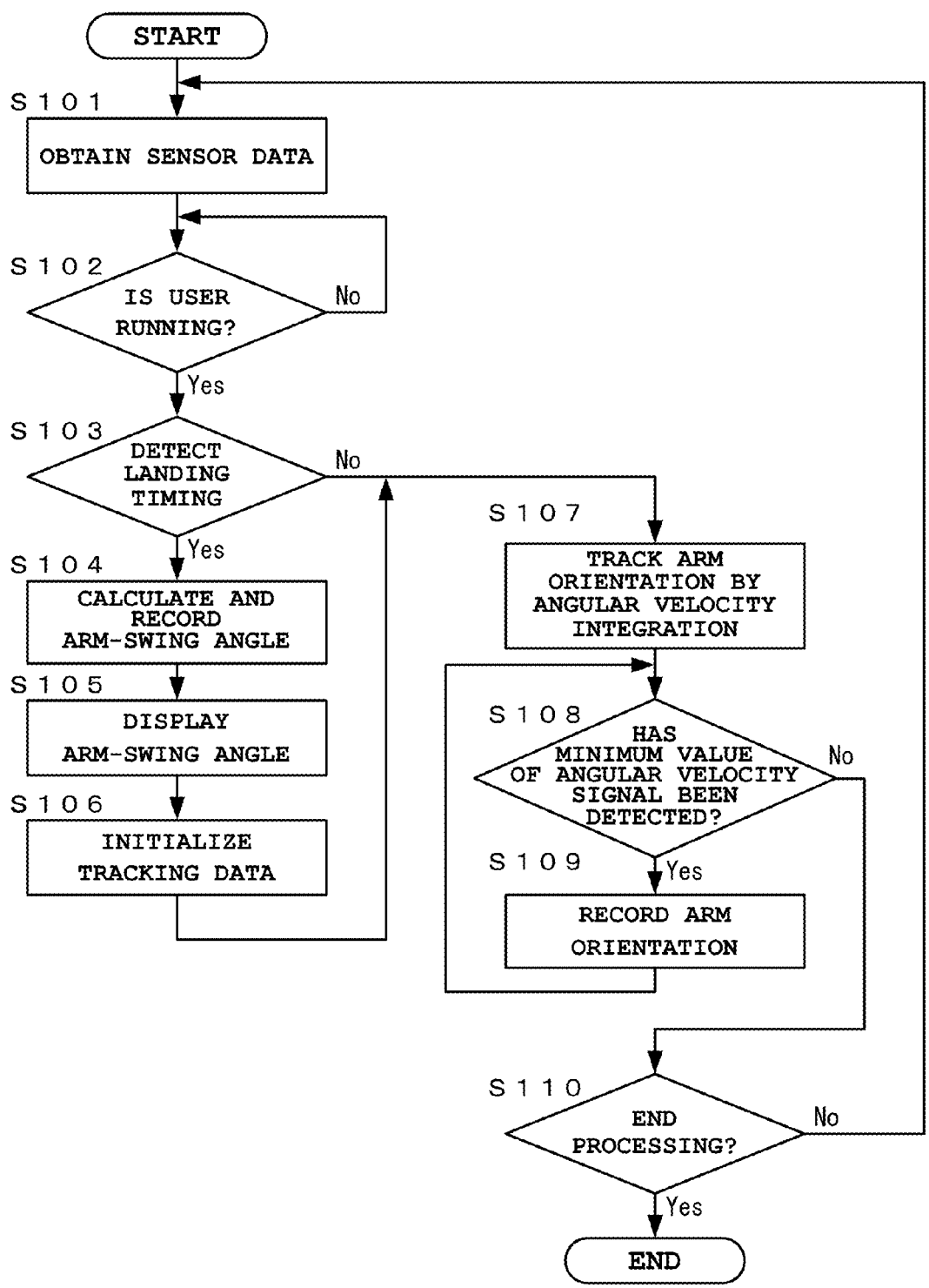
FIG. 4 is a flowchart depicting an example of arm-orientation detection processing that is performed in the exercise support method according to the first embodiment.

FIG. 4 is a flowchart depicting an example of arm-orientation detection processing that is performed in the exercise support method according to the present embodiment.

FIG. 5A and FIG. 5B are waveform diagrams each depicting an example of the signal waveform of sensor data obtained in the exercise support method according to the present embodiment.

Figure 6A:
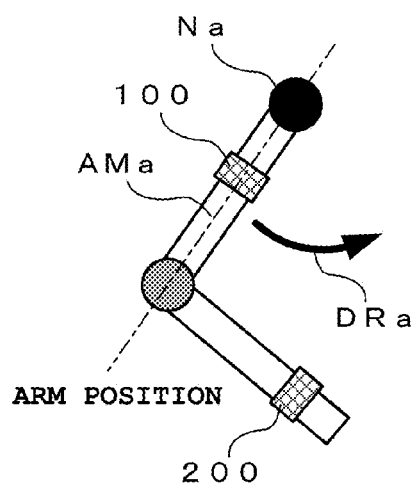
FIG. 6A and FIG. 6B are conceptual diagrams depicting an arm-orientation tracking operation (arm-swing status detecting operation) that is performed in the exercise support method according to the first embodiment.
Figure 6B:
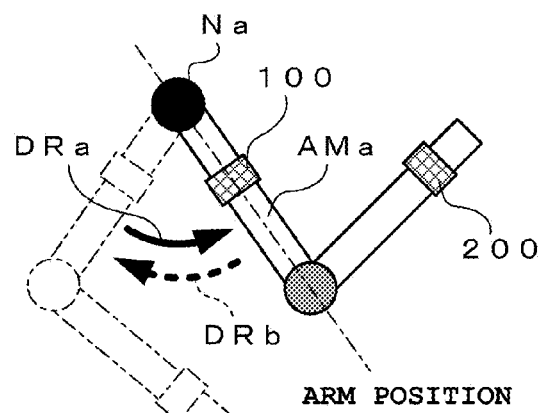

FIG. 6A and FIG. 6B are conceptual diagrams depicting an arm-orientation tracking operation (arm-swing status detecting operation) that is performed in the exercise support method according to the present embodiment.

Figure 7:
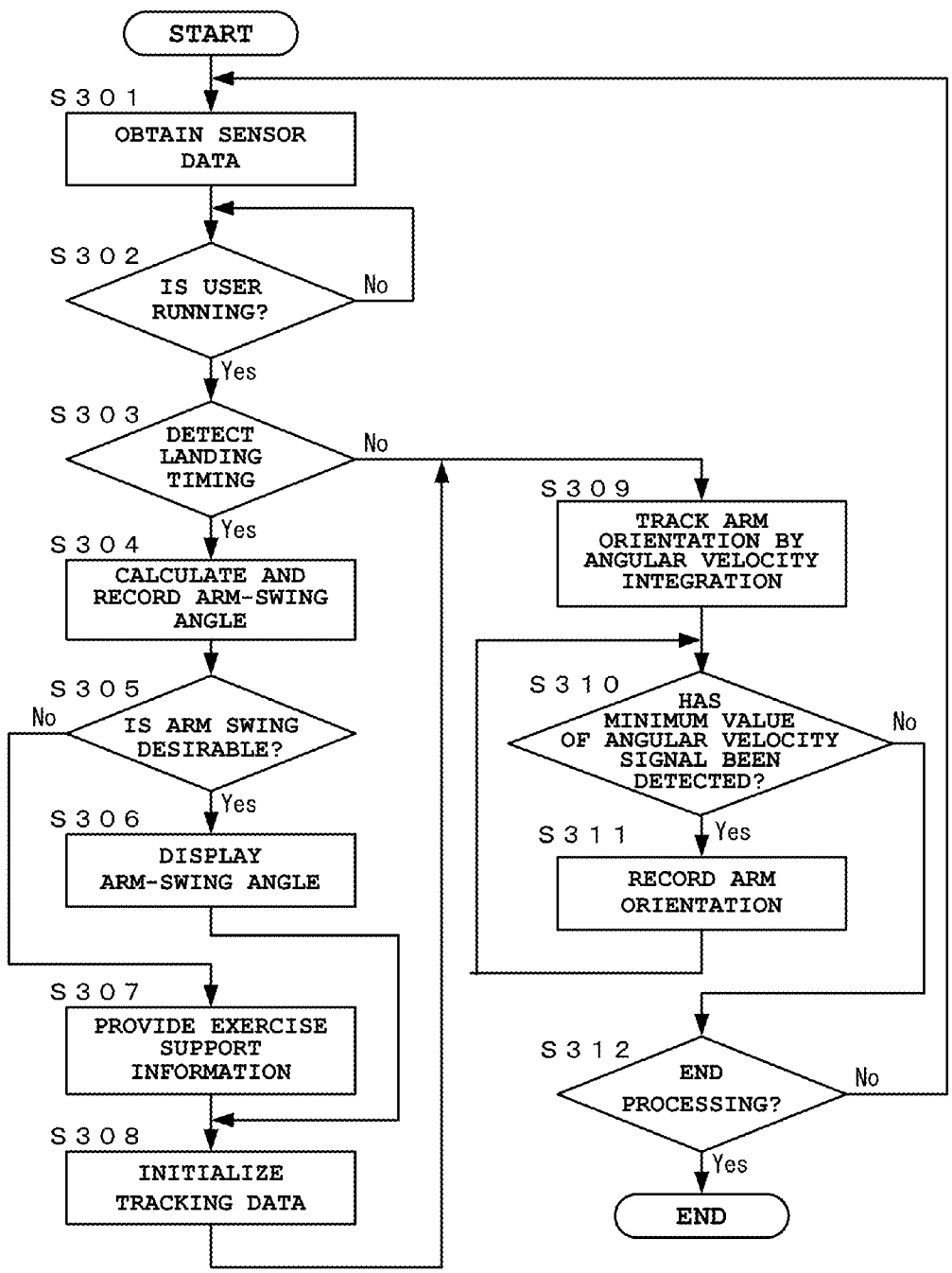
FIG. 7 is a flowchart depicting an example of arm-swing status judgment and support processing that is performed in the exercise support method according to the first embodiment.

FIG. 7 is a flowchart depicting an example of arm-swing status judgment and support processing that is performed in the exercise support method according to the present embodiment.

In the exercise support method according to the present embodiment, mainly, arm-orientation detection processing (Step S100), arm-swing evaluation processing (Step S200), and arm-swing status judgment and support processing (Step S300) are sequentially performed, as depicted in FIG. 3.

Here, the arm-swing status judgment and support processing (Step S300) is performed when the user is making a running motion for the second time or later, after the arm-orientation detection processing (Step S100) and the arm-swing evaluation processing (Step S200) are performed at least once.

That is, the arm-swing status judgment and support processing is an operation to be performed with arm-swing angle data regarding previous running motions and evaluation information (label) provided to the arm-swing angle data being stored in the memory section 160.

(Arm-Orientation Detection Processing)

In the arm-orientation detection processing (Step S100), the user US first operates power switches of the terminal 100 and the terminal 200 worn on the body, and thereby starts the terminal 100 and the terminal 200.

Next, before or after starting a running motion, the user US operates the input operating section 130 of the terminal 100 and the input operating section 220 of the terminal 200, and thereby starts a sensing operation in the terminal 100 and various information notifying operations in the terminal 200.

As a result, in the terminal 100 worn on an upper arm portion of the user US, acceleration data during the exercise motion is detected by the acceleration sensor 110 as appropriate, and angular velocity data is detected by the angular velocity sensor 120 as appropriate, as depicted in the flowchart of FIG. 4.

The arithmetic circuit 150 obtains these sensor data from the acceleration sensor 110 and the angular velocity sensor 120 as appropriate, and stores the respective sensor data in association with temporal data in a predetermined storage area of the memory section 160 (data memory) (Step S101).

Here, the acceleration data obtained at Step S101 has a signal waveform such as that depicted in FIG. 5A. FIG. 5A represents temporal changes of combined acceleration obtained by the arithmetic circuit 150 combining signal components corresponding to respective accelerations in triaxial directions in acceleration data outputted from the acceleration sensor 110.

The angular velocity data obtained at Step S101 has a signal waveform such as that depicted in FIG. 5B. FIG. 5B represents temporal changes of combined angular velocity obtained by the arithmetic circuit 150 combining signal components corresponding to respective angular velocities in triaxial directions in angular velocity data outputted from the angular velocity sensor 120.

As evident from the signal waveforms depicted in FIG. 5A and FIG. 5B, in the signal waveforms of combined acceleration and combined angular velocity exerted on a human body at the time of running, a maximum value and a minimum value appear in an approximately constant cycle. The appearance timing of the maximum value and the minimum value of the combined acceleration and that of the maximum value and the minimum value of the combined angular velocity have a close correspondence relationship with each other.

Next, the arithmetic circuit 150 judges whether or not the user US is running based on the obtained acceleration data (Step S102).

Specifically, the judgment at Step S102 as to whether or not the user US is running is made based on whether or not the combined acceleration depicted in FIG. 5A has a signal waveform unique to running.

That is, it is known that a characteristic change with a specific cycle, intensity, and the like is observed in the signal waveform of combined acceleration at the time of running. Therefore, by observing the signal waveform of the combined acceleration and judging whether or not the characteristic change at the time of running is observed in this signal waveform, it is possible to accurately judge whether or not the user US is running.

Note that the processing for judging whether or not the user US is running is not limited to the above-described method. For example, the arithmetic circuit 150 may judge whether or not the user US is running by previously registering the acceleration data of the user's previous running exercise and comparing it with the acceleration data obtained at Step S101.

Next, when judged at Step S102 that the user US is running (Yes at Step S102), the arithmetic circuit 150 detects foot landing timing in the running motion (Step S103).

Conversely, when judged at Step S102 that the user US is not running (No at Step S102), the arithmetic circuit 150 continues the observation of the combined acceleration.

Specifically, the detection of foot landing timing at Step S103 is performed based on the signal waveform of the combined acceleration depicted in FIG. 5A.

The signal waveform of the combined acceleration cyclically has a maximum value, as depicted in FIG. 5A (indicated by being circled in the drawing). This maximum value can be regarded as coming from an impact when a foot of the user US lands (landing impact). Therefore, the arithmetic circuit 150 tracks the acceleration data detected as appropriate by the acceleration sensor 110, and detects timing at which the signal waveform of the combined acceleration has a maximum value as foot landing timing.

The detected foot landing timing serves as the start timing and the end timing of an operation period for one cycle in an arm-posture tracking operation to be performed at Step S107 described below.

Also, the arithmetic circuit 150 obtains information about a footstep count and pitch during the running based on the detection of the foot landing timing, and stores the obtained information in a predetermined storage area of the memory section 160 (data memory).

Here, the footstep count is obtained by counting the number of foot landing impacts, that is, foot landing timings. The pitch is obtained by counting a footstep per time.

When foot landing timing is not detected at Step S103 (No at Step S103), the arithmetic circuit 150 performs the processing operations of Step S107 and the subsequent steps described below.

When foot landing timing is detected at Step S103 (Yes at Step S103), the arithmetic circuit 150 calculates and obtains the angle of arm swing performed during a tracking operation for one cycle. Then, the arithmetic circuit 150 stores and records the obtained data regarding the arm-swing angle (arm-swing angle data) in a predetermined storage area of the memory section 160 (data memory) (Step S104).

Specifically, based on a plurality of data regarding arm orientation (hereinafter referred to as arm orientation data) recorded during a tracking operation period for one cycle at Step S109 described below, the arithmetic circuit 150 calculates and obtains a maximum value of differences between pieces of arm orientation data at two different timings as an arm-swing angle for one cycle. Then, the arithmetic circuit 150 stores the obtained data regarding the arm-swing angle in a predetermined storage area of the memory section 160.

This arm-swing angle is calculated based on a distance L from the shoulder joint (Na in FIG. 6A and FIG. 6B) to the angular velocity sensor 120 provided in the terminal 100 worn on the upper arm portion and an angular velocity ωt obtained based on the angular velocity data outputted from the angular velocity sensor 120 included in the terminal 100.

Here, the above-described arm-swing-angle calculation processing can be conceptually represented by Equation (1) further below.

That is, in the following Equation (1), an arm orientation recorded at Step S109 described below is taken as Ak (k=1 to n; n is a positive integer), an arm-swing angle obtained by calculation is taken as Output.

Then, with arm orientations at two different timings being taken as Ap and Aq (p, q=1 to n), an angle "angle (Ap, Aq)" representing a difference between two arm angles defined by the positions of the arm in the arm orientations Ap and Aq is calculated.

Then, processing for extracting a maximum value (max) of the calculated angle "angle (Ap, Aq)" as an arm-swing angle is performed.

Note that Equation (1) does not represent a specific function expression for performing arm-swing angle calculation processing but represents the concept of the processing.

$$\text{Output} = \max(\text{angle}(A_p, A_q)_{(p,q=1-n)}) \quad (1)$$

Next, the arithmetic circuit 240 causes the value of the arm-swing angle obtained by the arithmetic circuit 150 and the values of the footstep count and the pitch obtained by the arithmetic circuit 150 to be displayed on the display section 231 of the terminal 200 worn on the forearm portion as exercise motion information (Step S105).

Specifically, the arithmetic circuit 150 of the terminal 100 extracts from the memory section 160 the footstep count and the pitch obtained at Step S103 and the arm-swing angle obtained at Step S104, and transmits the extracted values to the terminal 200 via the communication circuit section 170.

Then, the arithmetic circuit 240 of the terminal 200 causes exercise motion information including these data received via the communication circuit section 210 to be displayed on the display section 231 in a predetermined display format.

Here, at Step S105, the value of the arm-swing angle to be displayed as exercise motion information on the display section 231 of the terminal 200 is not set at a value obtained immediately before this display operation but is set at a value obtained before one cycle or more from the current time point in an arm-orientation tracking operation performed at Step S107 described below. This is to prevent the display of a value of arm swing in a state different from a normal state when the user US is viewing the display section 231 of the terminal 200.

That is, in general, when viewing the display section 231 of the terminal 200 worn on the forearm portion, the user US temporarily stops the swing motion or makes a slight arm swing in order to read display content on the display section 231, whereby the arm-swing status becomes different from usual. As a result, the arm-swing angle obtained immediately before the display operation has a swing value in a state different from usual. Thus, the value of the arm-swing angle to be displayed on the display section 231 is set at a value obtained before one cycle or more from the current time point in a normal swing state.

Next, the arithmetic circuit 150 initializes the tracking data obtained in the arm-orientation tracking operation performed at Step S107 described below (Step S106).

Specifically, the arithmetic circuit 150 detects foot landing timing at Step S103 and thereby clears (deletes) the arm orientation data obtained by the tracking operation in the immediately previous cycle. Then, the arithmetic circuit 150 sets timing for starting a tracking operation for the next cycle such that the timing corresponds to the above-described foot landing timing.

Here, the timing for starting a tracking operation for the next cycle corresponds to timing for ending the tracking operation for the immediately previous cycle (that is, the tracking operation currently being performed).

When foot landing timing is not detected at Step S103 (No at Step S103), the arithmetic circuit 150 starts an operation of tracking (successively tracking) a change in the arm orientation (Step S107).

Here, the arithmetic circuit 150 sequentially integrates angular velocity data detected by the angular velocity sensor 120 with respect to time by taking the start timing as a base point, and thereby tracks a change in the arm orientation.

This tracking operation is performed with a period from one landing timing until the next landing timing is detected at Step S103, that is, a period for one footstep in the running motion as one cycle.

Tracking data (arm orientation data) obtained in an immediately previous cycle is initialized at Step S106 for each cycle.

Specifically, at Step S107, based on the signal waveform of the combined angular velocity depicted in FIG. 5B, the arithmetic circuit 150 obtains swing information regarding the position of the arm and the direction of arm swing during the running motion.

That is, by observing the angular velocity data in the triaxial directions and the signal waveform of the combined angular velocity, it is possible to accurately ascertain the arm-swing status during the exercise motion of the user US.

Thus, based on the integration value of the angular velocity data in the triaxial direction detected as appropriate by the angular velocity sensor 120 with respect to time, the arithmetic circuit 150 tracks the position of an upper arm AMa and the direction of arm swing when the shoulder joint Na is taken as a fulcrum, as depicted in FIG. 6A and FIG. 6B.

Here, when the angular velocity components of the angular velocity data in triaxial directions of x, y, and z orthogonal to each other are ωx, ωy, and ωz, respectively, an angular velocity ωt of the upper arm AMa when the arm is being swung can be represented by Equation (2) further below.

The arithmetic circuit 150 calculates, as appropriate, the angular velocity t at the time of arm swing based on the angular velocity data detected as appropriate by the angular velocity sensor 120.

$$\|\omega_t\| = \sqrt{\omega_x^2 + \omega_y^2 + \omega_z^2} \quad (2)$$

Then, the arithmetic circuit 150 detects timing at which the angular velocity ωt calculated as appropriate has a minimum value (Step S108).

Specifically, as depicted in FIG. 6B, the angular velocity ωt has a minimum value (=0) at timing corresponding to the end of arm swing when the upper arm AMa is fully swung to one direction (for example, a DRa direction in the drawing) and then the arm-swing direction is changed to a reverse direction (for example, a DRb direction in the drawing).

Thus, the arithmetic circuit 150 detects timing at which the angular velocity becomes a minimum value (indicated by being circled in the drawing) in the signal waveform of the combined angular velocity depicted in FIG. 5B.

Next, when a minimum value of the angular velocity ωt is detected at Step S108 (Yes at Step S108), the arithmetic circuit 150 obtains arm orientation at that timing and records the obtained arm orientation in sequence (Step S109).

Specifically, when judged that the angular velocity ωt has a minimum value, the arithmetic circuit 150 obtains arm orientation data including the position (angle) of the arm at that timing, and stores the obtained date in a predetermined storage area of the memory section 160. The arithmetic circuit 150 repeatedly performs this processing at Step S108 and Step S109.

Here, for Step S108 and Step S109, when the signal waveform of combined angular velocity such as that depicted in FIG. 5B is verified in detail, the angular velocity slightly fluctuates near the timing at which the angular velocity has a minimum value. In addition, the angular velocity may have a minimum value not only at the timing corresponding to an arm swing end where a swing direction of the user US is changed but also at a plurality of other timings.

In this case, it is difficult at Step S108 to judge which minimum value is a value caused by the change of a swing direction at an arm swing end while the angular velocity is continuously fluctuating.

In the present embodiment, at Step S109, the arithmetic circuit 150 obtains and records a plurality of arm orientations at a plurality of timings (indicated by being circled in FIG. 6B) when the angular velocity has a minimum value. Here, a judgment is not made regarding which minimum value, among the plurality of minimum values, is a value caused by the change of an arm swing direction at an arm swing end.

Here, at Step S104, the arithmetic circuit 150 calculates a maximum value of differences between two pieces of arm orientation data at two different timings from among the plurality of arm orientation data obtained and recorded during the tracking operation period for one cycle at Step S109, as described above.

Thus, it is not required to judge which minimum value, among the plurality of minimum values, is a value caused by the change of a swing direction at an arm swing end.

On the other hand, when a minimum value of the angular velocity ωt is not detected at Step S108 (No at Step S108), the arithmetic circuit 150 returns to Step S101, and repeatedly performs the series of processing operations at Step S101 to Step S109 until the user US operates the input operating section 130 of the terminal 100 or the input operating section 220 of the terminal 200 to end the sensing operation or turn off the power (No at Step S110).

When the user US operates the input operating section 130 of the terminal 100 or the input operating section 220 of the terminal 200 to end the sensing operation or perform an operation of turning off the power (Yeas at Step S110), the series of processing operations described above ends.

When the inventor performed a verification experiment on this arm-orientation detection processing, a coefficient of correlation between an arm-swing angle estimated from an image of the user US captured at the time of running and an arm-swing angle estimated based on angular velocity data detected by the angular velocity sensor worn on an upper arm portion of the user US based on the series of processing operations described above has an extremely high value exceeding 0.95.

Therefore, it has been found that an arm-swing angle at the time of running can be accurately obtained by the method according to the present embodiment.

In the above-described arm-orientation detection processing, the timing at which acceleration data has a maximum value is taken as foot landing timing at Step S103. However, the present invention is not limited thereto.

For example, when the signal waveform of acceleration such as that depicted in FIG. 5A is verified in detail, the acceleration slightly fluctuates at timing other than timing at which the acceleration has a maximum value due to foot landing, and maximum values may be present at a plurality of timings.

In this case, by calculating or extracting timing which satisfies a condition that, for example, the acceleration has a maximum value equal to or larger than a predetermined threshold (for example, 40 m/s$^2$) or that the acceleration has a maximum value and a time change amount (a time derivative) is equal to or larger than a predetermined value, an accurate foot landing timing can be detected.

Also, at Step S104, the arm-swing angle obtained by the arithmetic circuit 150 is set at a maximum value of differences of the arm orientation data (arm angles) at two different timings among the plurality of timings at which the angular velocity ωt has a minimum value at Step S108 and Step S109. However, the present invention is not limited to this method.

For example, the arm-swing angle may be set at an angle corresponding to a difference between a maximum value of an angle of the arm in the anterior direction (the DRa direction depicted in FIG. 6A) found by time integration of the angular velocity data and a maximum value of an angle in the posterior direction (the DRb direction depicted in FIG. 6B).

Moreover, at Step S105, as a method for avoiding the influence to an arm-swing angle due to the user US temporarily stopping an arm swing motion or swinging the arms slightly so as to view exercise motion information displayed on the display section 231 of the terminal 200, a method of displaying a value obtained before one cycle or more from the current time point is described. However, the present invention is not limited to this scheme.

For example, a method may be applied in which an acceleration sensor incorporated in the terminal 200 detects whether or not the arm is in a state where the user US is viewing the display section, and display update is stopped or a value obtained before one cycle or more from the current time point is displayed only when the user US is detected to be viewing the display section.

Specifically, the magnitude of acceleration in a vertical direction is significantly large during a running motion. On the other hand, when making a motion of viewing the display section 231 of the terminal 200, the user US is required to at least lift the forearm portion to move the terminal 200 and achieve a position and angle at which the user US can view the display section 231, in order to read the display contents of the display section 231. Therefore, when the display section 231 is to be viewed during a running motion, acceleration in the perpendicular direction with respect to the plane including the display section 231 is increased (first operation condition). In addition, in this case, since the arm-lifted state is temporarily maintained, change in the arm orientation is decreased, and the magnitude of the angular velocity is decreased (second operation condition). Thus, when the states of the first and second operation conditions are simultaneously detected, the user US is judged to be viewing the display section 231 of the terminal 200 during a running motion, and therefore update of the display of the arm-swing angle in the display section 231 is stopped or a value obtained before one cycle or more from the current time point is displayed.

Furthermore, at Step S105, as a method for notifying the user US of the exercise motion information including the arm-swing angle, a method of displaying the exercise motion information on the display section 231 of the terminal 200 is applied. However, the present invention is not limited to this scheme.

That is, it is only required that the user US is suitably provided with the exercise motion information by this notifying operation. Accordingly, for example, a configuration may be adopted in which the notification of the exercise motion information is performed by audio information, alarm sound, or the like from the acoustic section provided in the terminal 100 or the terminal 200, in addition to or in place of display on the display section 231. Alternatively, a configuration may be adopted in which notification is performed by using vibration information from the vibrating section.

Still further, at Step S107, the foot landing timing at which the acceleration has a maximum value is set as the timing of starting (or ending) an operation of tracking a change in arm orientation. However, the present invention is not limited thereto.

That is, it is only required that the operation period of a tracking operation for one cycle is a period corresponding to one cycle of a swing motion. Accordingly, for example, a configuration may be adopted in which arbitrary timing shifted (elapsed) by a predetermined time from the foot landing timing is set as tracking-operation start and end timing.

(Arm-Swing Evaluation Processing)

In the arm-swing evaluation processing (Step S200), after the end of the running motion, the arm-swing angle obtained by the above-described arm-orientation detection processing during this motion and stored in the memory section 160 of the terminal 100 is displayed on the display section 231 of the terminal 200 or the display section 140 of the terminal 100.

Here, the arm-swing angle obtained by the above-described arm-orientation detection processing in each cycle is displayed on the display section 231 or the display section 140 in a list format, a graph format, or the like.

Next, the user US views the arm-swing angles displayed on the display section 231 or the display section 140, and provides each arm-swing angle with subjective evaluation information regarding, for example, whether the condition at the time of the running motion is desirable or not.

Then, the arithmetic circuit 150 of the terminal 100 stores the evaluation information in association with the arm-swing angle in a predetermined storage area of the memory section 160.

Note that the arithmetic circuit 150 may provide the arm-swing angle with circumstance information regarding temperature, wind velocity, and road condition at the time of the running exercise and associate the information with the arm-swing angle for storage in a predetermined storage region of the memory section 160.

(Arm-Swing Status Judgment/Support Processing)

The arm-swing status judgment/support processing (Step S300) is an operation that is performed when the user is making a running motion for the second time or later, as described above.

In the following, descriptions of operations equivalent to those in the above-described arm-orientation detection processing (Steps S101 to S110) are simplified or omitted.

In the arm-swing status judgment/support processing, as depicted in the flowchart of FIG. 7, the user US first starts the terminal 100 and the terminal 200 as in the case of Step S101 to Step S104 depicted in the arm-orientation detection processing (refer to FIG. 4). As a result, acceleration data during an exercise motion is detected by the acceleration sensor 110 as appropriate, and angular velocity data is detected by the angular velocity sensor 120 as appropriate (Step S301).

Next, based on the obtained acceleration data, the arithmetic circuit 150 judges whether or not the user US is running (Step S302).

When judged at Step S302 that the user US is running (Yes at Step S302), the arithmetic circuit 150 detects foot landing timing (Step S303).

The foot landing timing detected herein serves as start timing (or end timing) in the arm-orientation tracking operation which is performed at Step S309 described below.

Next, when foot landing timing is detected at Step S303 (Yes at Step S303), the arithmetic circuit 150 calculates and obtains, as an arm-swing angle in one cycle, a maximum value of differences of arm orientation data at two different timings form among a plurality of arm orientation data recorded during a tracking operation period for one cycle at Step S311 described below. Then, the arithmetic circuit 150 stores the obtained arm-swing angle data in the memory section 160 (Step S304).

Next, the arithmetic circuit 150 compares the arm-swing angle obtained at Step S304 and an arm-swing angle evaluated as desirable by the user US in the above-described arm-swing evaluation processing and stored in the memory section 160 (Step S200), and thereby judges whether or not the arm swing is desirable (Step S305).

Note that whether or not the arm swing is desirable may be judged further based on evaluation information acquired in a circumstance similar to that at the time of the obtainment of the arm-swing angle.

When judged at Step S305 that the obtained arm-swing angle and the arm-swing angle evaluated as desirable are equal or equivalent to each other and the current arm orientation is desirable (Yes at Step S305), the arithmetic circuit 150 causes the values of a footstep count and pitch based on the sensor data obtained by the terminal 100 and the above-described arm-swing angle to be displayed as exercise motion information on the display section 231 of the terminal 200 worn on the forearm portion (Step S306).

On the other hand, when judged at Step S305 that the obtained arm-swing angle and the arm-swing angle evaluated as desirable are not equal or equivalent to each other and the current arm orientation is not desirable (No at Step S305), the arithmetic circuit 150 notifies the user US of the obtained arm-swing angle together with the judgment result and the exercise support information for correcting the current arm orientation (Step S307).

Specifically, for example, when the obtained arm-swing angle is smaller than the arm-swing angle evaluated as desirable in the arm-swing evaluation processing, the arithmetic circuit 150 causes the obtained arm-swing and, for example, a message such as "Your arm swing is too short" (judgment result) to be displayed on the display section 231 of the terminal 200 to notify the user US thereof.

Alternatively, in the case described above, the arithmetic circuit 150 causes a message (the exercise support information such as warning or caution) such as "Swing your arm longer" to be displayed on the display section 231 of the terminal 200 to prompt a large arm-swing angle and guide the current arm orientation to an appropriate state (desirable arm orientation), and thereby notifies the user US thereof.

Here, as a method for displaying the exercise motion information and the exercise support information at Step S306 and Step S307, a method may be adopted in which multiple pieces of information set in advance are simultaneously displayed on the display section 231. Alternatively, a method may be adopted in which multiple pieces of information are sequentially displayed. Still alternatively, a method may be adopted in which desired pieces of information are simultaneously or sequentially displayed by the user US operating the input operating section 220.

Also, as a method for notifying the user US of the exercise motion information and the exercise support information, a method may be adopted in which the acoustic section 232 notifies the user US by using audio information or alarm sound, or the vibrating section 233 notifies the user US by using vibration information, in addition to or in place of display on the display section 231.

Next, the arithmetic circuit 150 initializes the tracking data obtained in the arm-orientation tracking operation performed at Step S309 described below (Step S308).

As a result, the arithmetic circuit 150 clears the arm orientation data obtained by the tracking operation in the immediately previous cycle. The arithmetic circuit 150 then sets timing for starting a tracking operation for the next cycle, corresponding to the above-described foot landing timing.

When foot landing timing has not been detected at Step S303 (No at Step S303), the arithmetic circuit 150 integrates the angular velocity data detected by the angular velocity sensor 120 with respect to time, and thereby starts an operation of tracking a change in arm orientation for one cycle corresponding to a period of one footstep in the running motion (Step S309).

Then, the arithmetic circuit 150 detects timing at which angular velocity calculated as appropriate has a minimum value (Yes at Step S310).

Next, when a minimum value of the angular velocity is detected at Step S310, the arithmetic circuit 150 obtains arm orientation data including the position (angle) of the arm at that timing and records the obtained data in sequence (Step S311).

Hereafter, the arithmetic circuit 150 repeatedly performs the processing at Step S310 and Step S311.

At Step S310, when a minimum value of the angular velocity is not detected (No at Step S310), the arithmetic circuit 150 returns to Step S301, and repeatedly performs the series of processing operations at Step S301 to Step S311 until the user US ends the sensing operation in the terminal 100 or turns off the power (No at Step S312).

When the user US ends the sensing operation in the terminal 100 or performs an operation of turning off the power (Yes at Step S312), the series of processing operations described above ends.

Note that, although the method is described at Step S304 and Step S305 in which whether the arm orientation is desirable or not is judged based on the obtained arm-swing angle, the present invention is not limited thereto.

For example, a method may be adopted in which the arithmetic circuit 150 finds the temporal change of an arm-swing angle during a running motion, and judges whether or not this change of the arm-swing angle is within a predetermined range evaluated in advance as having a desirable arm orientation.

In this case, when the current change of the arm-swing angle is not within the predetermined range, the user US is notified of the exercise support information such as warning or caution, as described above.

As described above, in the present embodiment, the arithmetic circuit 150 first judges whether or not the user is running based on sensor data detected by the acceleration sensor 110 and the angular velocity sensor 120 incorporated in the terminal 100 worn on the upper arm portion of the body.

Then, when judged that the user US is running, the arithmetic circuit 150 performs processing for tracking a change in arm orientation (that is, angular velocity) with timing at which foot landing is detected as start timing.

As a result, an arm orientation at each timing when the angular velocity has a minimum value is recorded, and evaluation information is provided to an arm-swing angle with a maximum value of differences of arm orientation data at two different timings in a period corresponding to one cycle of the arm-swing motion.

Next, based on the arm-swing angle provided with the evaluation information, the arithmetic circuit 150 makes a comparison with an arm-swing angle obtained in the next exercise motion or later. Then, based on the comparison result, the arithmetic circuit 150 notifies the user of the exercise support information to guide the user to an appropriate arm orientation status.

Therefore, in the present embodiment, it is possible to output an index allowing an accurate judgment to be made as to by which degrees the user is swinging arms when performing an exercise such as a running exercise. As a result, the exercise motion status including the arm-swing angle can be suitably transmitted to the user. Also, exercise support for guiding the user to an appropriate exercise motion status can be provided.

In particular, during the motion of an exercise such as a running exercise, the arm-swing angle is updated as needed every time foot landing is detected. Accordingly, the exercise motion status including the arm-swing angle can be obtained almost in real time, and the user can be notified of the obtained exercise motion status together with the exercise support information.

Thus, the temporal change of an arm-swing angle and arm orientation, whether or not a stable arm swing is being performed (that is, whether variations in an arm-swing angle are significant or not), a difference from the swing of arms in a good condition, and the like can be obtained in real time and judged. Also, the user can be quickly notified of an improvement method for achieving an appropriate exercise motion status (for example, the user US is notified to swing his or her arms longer).

In the present embodiment, the terminal for notifying the user of exercise motion information and the exercise support information has an outer appearance and shape of a wristwatch that is worn on a forearm portion (wrist) of a human body, which allows the user to favorably obtain exercise motion information including a footstep count, pitch, and an arm-swing angle even while the user is exercising, without making the user particularly aware of this obtainment.

With this terminal, even when an operation of viewing the display section is performed, the user is notified of a value obtained before one cycle or more from the current time point. Therefore, the change in the arm-swing status when the user US is viewing the display section does not affect the exercise motion information and the exercise support information.

Second Embodiment

Next, a second embodiment of the exercise support device according to the present invention is described.

The exercise support device described in the first embodiment has the terminal 100 which is worn on an upper arm portion of a human body and the terminal 200 which is worn on a forearm portion. In the terminal 100 worn on the upper arm portion, an exercise motion status including an arm-swing angle when the user US is exercising is ascertained based on sensor data obtained by the acceleration sensor 110 and the angular velocity sensor 120. Then, by the terminal 200 worn on the forearm portion, the user US is notified of exercise motion information and the exercise support information based on the exercise motion information.

In the second embodiment, in a single terminal mounted on an upper arm portion or a forearm portion, an exercise motion status including an arm-swing angle when the user US is exercising is ascertained, and the user US is notified of exercise motion information and the exercise support information.

Figure 8A:
FIG. 8A and FIG. 8B are schematic structural diagrams depicting an exercise support device according to a second embodiment of the present invention.
Figure 8B:

FIG. 8A and FIG. 8B are schematic structural diagrams depicting the exercise support device according to the second embodiment. FIG. 8A is a schematic diagram depicting a state where the exercise support device according to the present embodiment has been worn on an upper arm portion of a human body (first example), and FIG. 8B is a schematic diagram depicting a state where the exercise support device according to the present embodiment has been worn on a forearm portion of a human body (second example).

Figure 9:
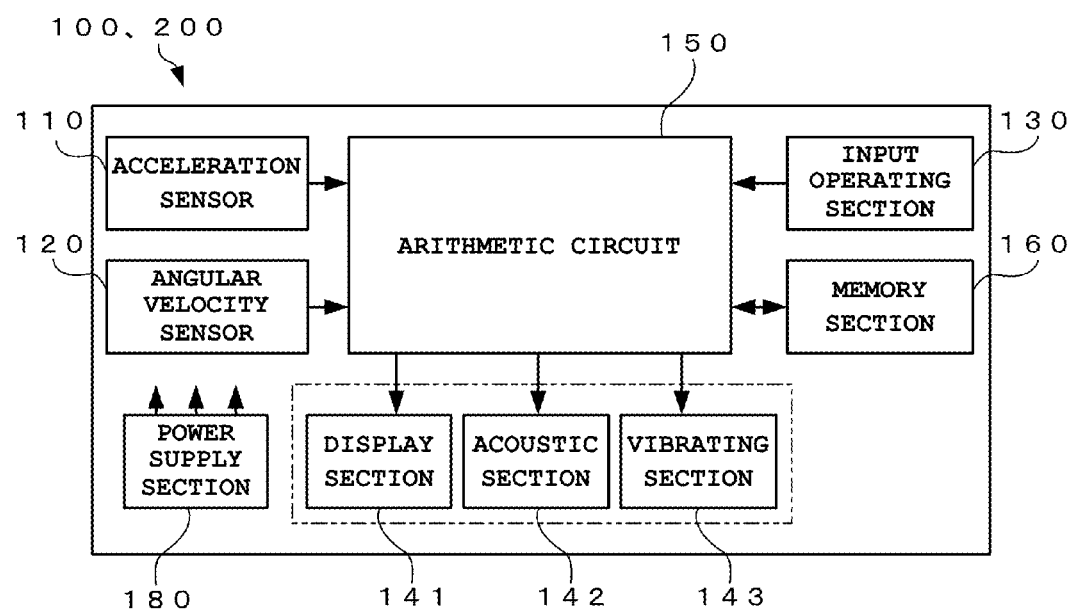
FIG. 9 is a functional block diagram depicting an example of the structure of the exercise support device according to the second embodiment.

FIG. 9 is a functional block diagram depicting an example of the structure of the exercise support device according to the present embodiment.

FIG. 10A, FIG. 10B, FIG. 10C and FIG. 10D are conceptual diagrams depicting an arm-orientation tracking operation (arm-swing status detecting operation) to be performed in a exercise support method according to the second embodiment.

Note that, here, sections and processing equivalent to those described in the first embodiment are provided with the same reference numerals, and explanations thereof are simplified or omitted.

As in the case of the first embodiment (refer to FIG. 1B), the exercise support device according to the first example of the present embodiment has an outer appearance and shape of an upper-arm-worn type (or an armband type), and includes only the terminal 100 that is worn on an upper arm portion of the user US, as depicted in FIG. 8A.

As with the first embodiment (refer to FIG. 1C), an exercise support device 200 according to the second example of the present embodiment has an outer appearance and shape of a forearm-worn type (or a wristwatch type), and includes only the terminal 200 that is worn on a forearm portion (wrist) of the user US, as depicted in FIG. 8B.

Specifically, the terminal 100 or 200 mainly includes, for example, the acceleration sensor (detecting section) 110, the angular velocity sensor (detecting section) 120, the input operating section 130, a display section (information notifying section) 141, an acoustic section (information notifying section) 142, a vibrating section (information notifying section) 143, the arithmetic circuit (motion status judging section, arm-swing-angle calculating section, arm-swing status judging section, information notifying section) 150, the memory section 160, and the power supply section 180, as depicted in FIG. 9.

That is, the terminal 100 or 200 according to the present embodiment is a device having one housing, and is structured to have both the function for ascertaining and judging an exercise motion status including an arm-swing angle in the terminal 100 and the function for notifying the user US of exercise motion information and the exercise support information by the terminal 200 described in the first embodiment.

Although not depicted in the drawing, the terminals 100 and 200 may further include a communication circuit section for transmitting and receiving predetermined data via wired or wireless communication with an external device (for example, a personal computer, a tablet terminal, or a smartphone (a high-functionality portable telephone)).

In this exercise support device as well, as with the exercise support method described in the first embodiment, timing corresponding to an arm swing end is judged based on a change in angular velocity ωt calculated based on angular velocity data, as depicted in FIG. 10A to FIG. 10D.

Here, the timing corresponding to an arm swing end is timing at which the upper arm AMa is fully swung to one direction (for example, the DRa direction in the drawing) with the shoulder joint Na as a fulcrum and then the arm swing direction is changed to a reverse direction (for example, the DRb direction in the drawing).

Then, during a tracking operation period for one cycle, based on a plurality of arm orientation data obtained at a plurality of timings at which the angular velocity ωt has a minimum value, a maximum value of differences of arm orientation data at two different timings is obtained as an arm-swing angle in that one cycle.

Therefore, in the present embodiment as well, as with the above-described first embodiment, it is possible to accurately ascertain and judge by which degrees arms are being swung during the motion of an exercise such as a running exercise. Accordingly, an exercise motion status including an arm-swing angle can be suitably transmitted to the user, and exercise support can be made for guiding the user to an appropriate exercise motion status.

In particular, in the present embodiment, a single terminal is configured to have both the function for ascertaining and judging an exercise motion status including an arm-swing angle when the user US is exercising and the function for notifying the user US of exercise motion information and the exercise support information. Therefore, the number of devices to be worn on the body can be decreased, and burdens at the time of wearing devices and at the time of input operation can be reduced.

Figure 10A:
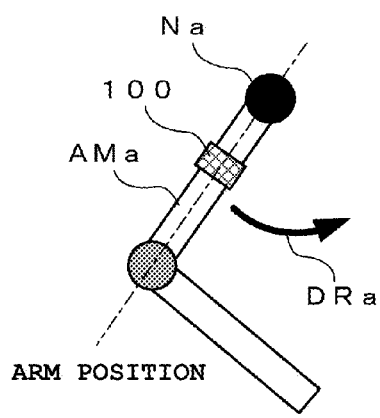
FIG. 10A, FIG. 10B, FIG. 10C and FIG. 10D are conceptual diagrams depicting an arm-orientation tracking operation (arm-swing status detecting operation) that is performed in a exercise support method according to the second embodiment.
Figure 10B:
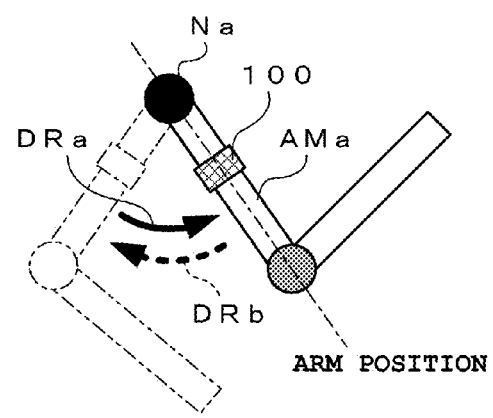

Here, in the first example of the present embodiment, the terminal 100 is worn on the upper arm portion AMa, as depicted in FIG. 8A, FIG. 10A and FIG. 10B. Therefore, if the information notifying method of displaying exercise motion information including an obtained arm-swing angle and the exercise support information based on the exercise motion information on the display section 141 is applied, it may be impossible or difficult for the user US to view the display section 141 during an exercise motion.

In this case, in the present embodiment, audio information, alarm sound, or the like is emitted from the acoustic section 142 or vibration information is generated from the vibrating section 143 in addition to or in place of display on the display section 141, whereby the user US can be suitably notified of the exercise motion information and the exercise support information.

Figure 10C:
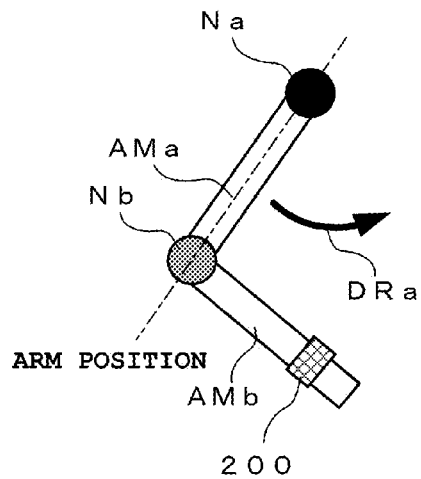
Figure 10D:
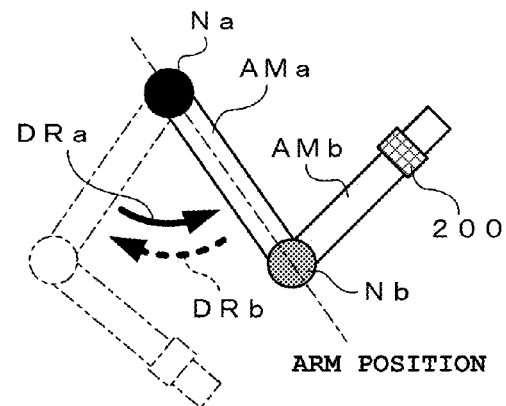

In the second example of the present embodiment, the terminal 200 including the acceleration sensor 110 and the angular velocity sensor 120 is worn on the forearm AMb connected to the shoulder joint Na via the upper arm AMa and an elbow joint Nb, as depicted in FIG. 8B, FIG. 10C and FIG. 10D. Therefore, compared with the case where the position (angle) and the angular velocity of the upper arm AMa directly connected to the shoulder joint Na are detected as described in the first embodiment and the first example of the present embodiment, the accuracy of estimating an arm-swing angle may be degraded.

In this case, in the present embodiment, by a component unique to the arm swing motion of a forearm portion during the motion of an exercise such as a running exercise being measured or estimated, and the detected angle and angular velocity of the arm being corrected as appropriate, the arm-swing angle can be relatively accurately estimated. As a result, the user can be notified of suitable exercise motion information and the exercise support information.

Third Embodiment

Next, a third embodiment of the exercise support device according to the present invention is described.

In the configuration of the exercise support device according to the first and second embodiments, an exercise motion status including a footstep count, pitch, and a arm-swing angle during the exercise motion of the user US is ascertained and judged by the terminal worn on an upper arm portion or a forearm portion of the body and the user US is notified of exercise motion information and the exercise support information.

In the third embodiment, the device is configured to store sensor data obtained from the terminal worn on a human body, a calculation result such as a footstep count and pitch, and various information such as an arm-swing angle and temporal change in arm orientation are stored in a stand-alone electronic device other than the terminal or an electronic device connected to a network.

Figure 11:
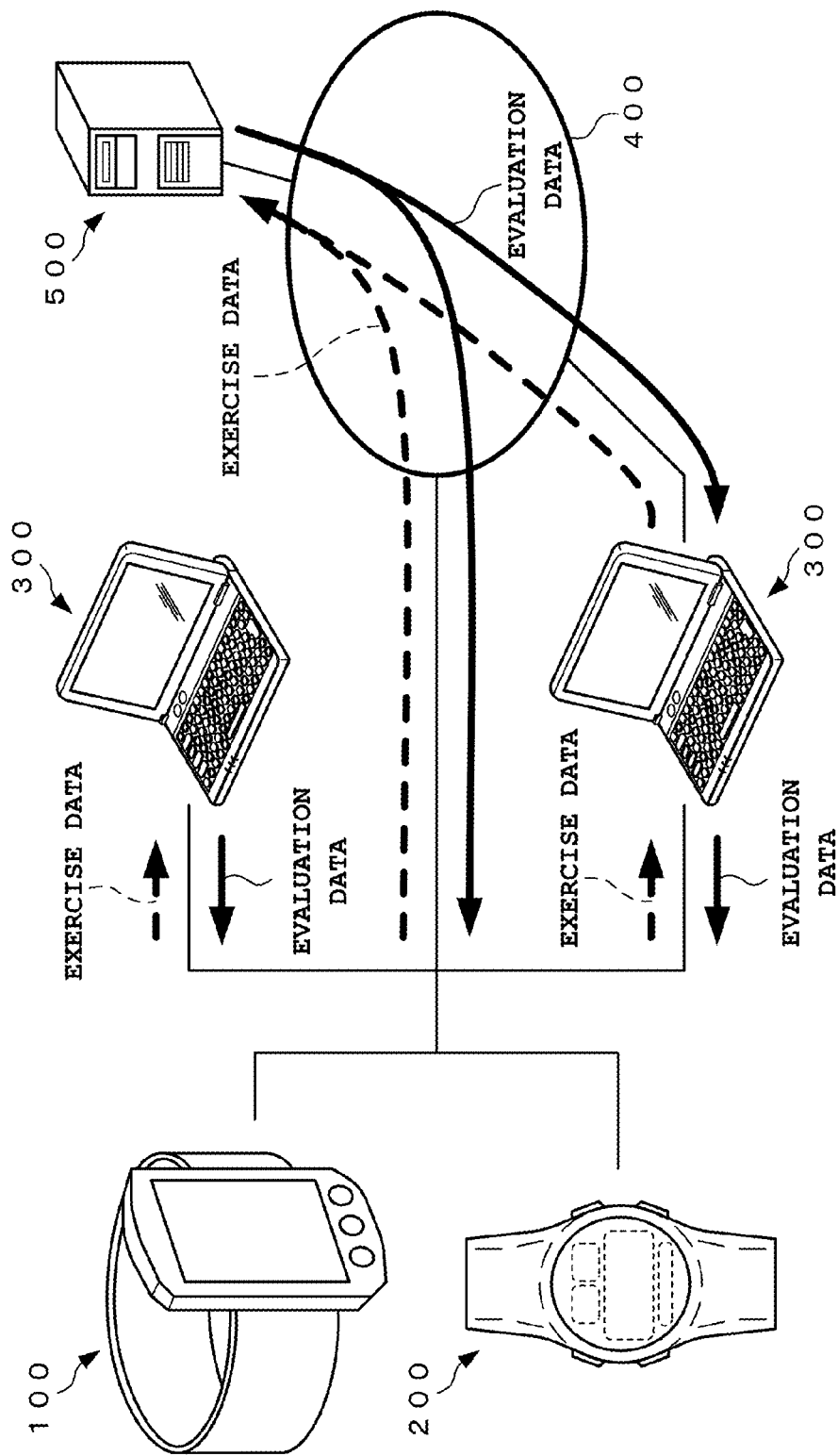
FIG. 11 is a schematic structural diagram depicting an exercise support device according to a third embodiment of the present invention.

FIG. 11 is a schematic structural diagram depicting the exercise support device according to the third embodiment.

Figure 12A:
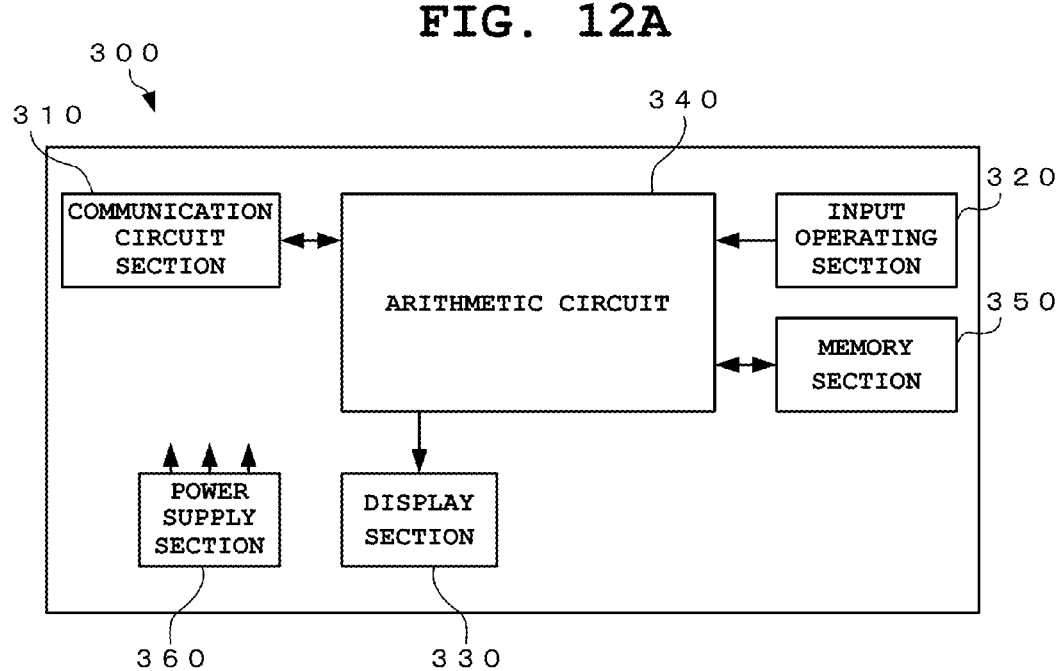
FIG. 12A and FIG. 12B are functional block diagrams each depicting an example of the structure of the exercise support device according to the third embodiment.
Figure 12B:
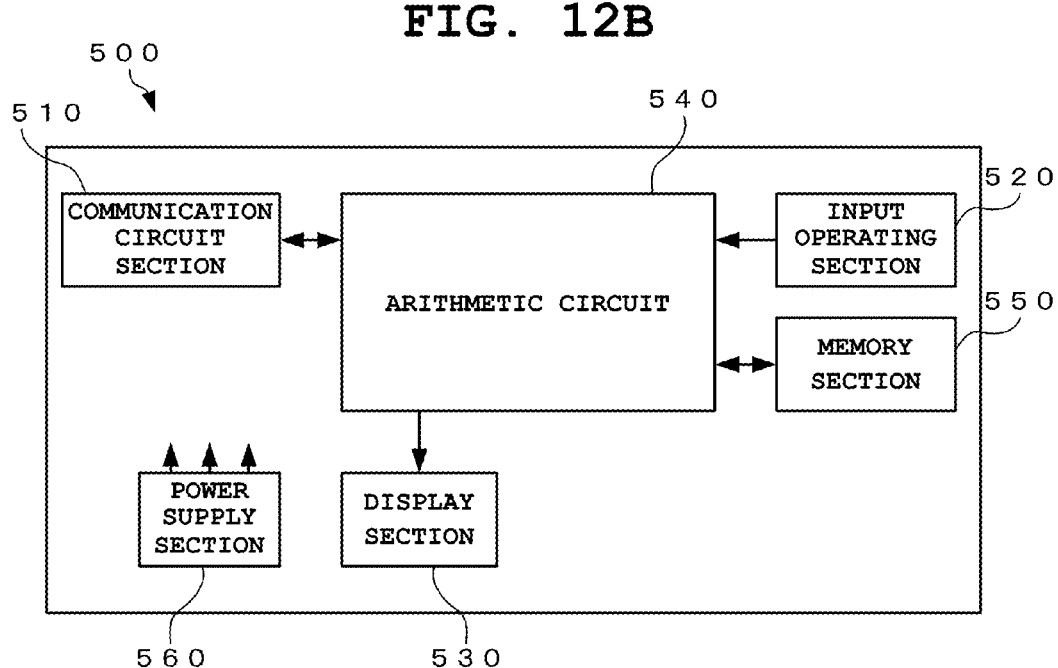

FIG. 12A and FIG. 12B are functional block diagrams each depicting an example of the structure of the exercise support device according to the present embodiment. FIG. 12A is a schematic structural diagram depicting an example of an information communication device applied to the exercise support device according to the present embodiment, and FIG. 12B is a schematic structural diagram depicting an example of a network server applied to the exercise support device.

Here, sections and processing equivalent to those described in the first and second embodiments are provided with the same reference numerals, and explanations thereof are simplified or omitted.

The exercise support device according to the third embodiment mainly includes, for example, the terminals 100 and 200, an information communication device 300, a network 400, and a network server 500, as depicted in FIG. 11.

Here, as with the above-described first and second embodiments, the terminals 100 and 200 have the function for obtaining a footstep count, pitch, and an arm-swing angle based on sensor data obtained during an exercise motion and the function for transmitting and receiving predetermined data from and to the information communication device 300 independently provided outside the terminals 100 and 200 and the network server 500 connected to the network 400.

The information communication device 300 is a device connected to the terminals 100 and 200 via wired or wireless communication and capable of data transmission and reception with the terminals 100 and 200. As the information communication device 300, a general-purpose device such as a notebook-type or desktop-type personal computer, a tablet terminal, or a smartphone, or a dedicated device is applied, as depicted in FIG. 11.

Specifically, the information communication device 300 mainly includes, for example, a communication circuit section 310, an input operating section 320, a display section 330, an arithmetic circuit 340, a memory section 350, and a power supply section 360, as depicted in FIG. 12A.

Here, the communication circuit section 310 functions as an interface when receiving sensor data obtained by the terminal 100 or 200 during an exercise motion and data regarding a footstep count, pitch, and an arm-swing angle (referred to as "exercise data" for convenience of explanation) based on the sensor data from the terminal 100 or 200.

Also, the communication circuit section 310 functions as an interface when transmitting exercise data received from the terminal 100 or 200 and provided with evaluation information by the user US (referred to as "evaluation data" for convenience of explanation) to the terminal 100 or 200.

Moreover, the communication circuit section 310 includes a function for connection to the network 400 such as the Internet or a LAN (Local Area Network), in addition to the function for transmitting and receiving exercise data and evaluation data to and from the terminal 100 or 200.

The arithmetic circuit 340 is an arithmetic device having a clocking function, and controls various operations such as an operation of transmitting exercise data and evaluation data and an operation for connection with the network 400 by the communication circuit section 310, an operation of storing and reading exercise data and evaluation data in and from the memory section 350, and an operation of displaying exercise data or the like by the display section 330, based on a predetermined operation clock.

The control program to be executed in the arithmetic circuit 340 may be stored in the memory section 350 or incorporated in advance in the arithmetic circuit 340.

The input operating section 320, the display section 330, and the power supply section 360 have functions equivalent to those of the input operating sections 130 and 220, the display sections 140, 141, and 231, and the power supply sections 180 and 260 of the terminals 100 and 200 in the above-described embodiments, and therefore explanations thereof are omitted.

The network server 500 is connected to the network 400 such that the terminals 100 and 200 can perform data transmission and reception directly or via the information communication device 300.

Specifically, the network server 500 mainly includes, for example, a communication circuit section 510, an input operating section 520, a display section 530, an arithmetic circuit 540, a memory section 550, and a power supply section 560, as depicted in FIG. 12B.

Here, the communication circuit section 510 has a function for connection to the network 400, and functions as an interface when exercise data transmitted from the terminal 100 or 200 is received directly via the network 400 or received via the information communication device 300 and the network.

Also, the communication circuit section 510 functions as an interface when evaluation data read out from the memory section 550 is transmitted to the terminal 100 or 200 via the network 400.

The arithmetic circuit 540 is an arithmetic device having a clocking function, and controls various operations such as an operation of transmitting exercise data and evaluation data, an operation of connecting to the network 400 by the communication circuit section 510, and an operation of storing and reading exercise data and evaluation data to and from the memory section 550, based on a predetermined operation clock.

The control program to be executed at the arithmetic circuit 540 may be stored in the memory section 550 or incorporated in advance in the arithmetic circuit 540.

The input operating section 520, the display section 530, and the power supply section 560 have functions equivalent to those of the input operating sections 130 and 220, the display sections 140, 141, and 231, and the power supply sections 180 and 260 of the terminals 100 and 200 described in the above-described embodiments, and therefore explanations thereof are omitted.

In this exercise support device, in the structure where the terminal 100 or 200 is connected only to the information communication device 300 via wired or wireless communication as depicted in FIG. 11, sensor data obtained during an exercise motion by the terminal 100 or 200 and exercise data such as a footstep count, pitch, and an arm-swing angle obtained based on the sensor data are transmitted to the information communication device 300 and stored in the memory 350.

By the exercise data stored in the information communication device 300 being displayed on the display section 330, the user US provides the arm-swing angle included in the exercise data with evaluation information indicating whether or not the condition is desirable, and the resultant data is stored as evaluation data in the memory 350.

Then, the evaluation data stored in the memory section 350 of the information communication device 300 is read out, transmitted via the communication circuit section 310 to the terminal 100 or 200, and stored in the memory section 160 or 250.

As a result, in the next and subsequent exercise motions, exercise data including an arm-swing angle obtained by the terminal 100 or 200 is compared based on the evaluation data transmitted from the information communication device 300. Then, based on the comparison result, the user US is notified of exercise motion information and the exercise support information.

Note that the evaluation processing for providing exercise data with evaluation information indicating whether or not the condition is desirable may be performed with the exercise data stored in the memory section 350 of the information communication device 300 being displayed on the display section 140, 141, or 231 of the terminal 100 or 200 connected via wired or wireless communication, and evaluation data after the provision of the evaluation information may be stored in the memory section 350 of the information communication device 300.

As depicted in FIG. 11, in the structure where the terminal 100 or 200 is connected to the network server 500 directly via the network 400 or via the information communication device 300 and the network 400 by wired or wireless communication, exercise data obtained by the terminal 100 or 200 during an exercise motion is transmitted to the network server 500 and stored in the memory section 550.

Subsequently, the user US uses the terminal 100 or 200 and the information communication device 300 to access the network server 500 via the network 400 and, with the exercise data stored in the memory section 550 being displayed on the display section 140, 141, or 231 of the terminal 100 or 200 and the display section 330 of the information communication device 300, provides evaluation information indicating whether or not the condition is desirable to an arm-swing angle included in the exercise data. Then, the resultant data is stored in the memory section 550 as evaluation data.

Next, the evaluation data stored in the memory section 550 of the network server 500 is read out, transmitted directly via the network 400 or via the network 400 and the information communication device 300 to the terminal 100 or 200, and stored in the memory section 160 and 250.

As a result, in the next and subsequent exercise motions, exercise data including an arm-swing angle obtained by the terminal 100 or 200 is compared based on the evaluation data transmitted from the network server 500. Then, based on the comparison result, the user US is notified of exercise motion information and the exercise support information.

Therefore, in this embodiment as well, the degree of arm swing during the motion of an exercise such as a running exercise can be accurately ascertained and judged, as in the case of the above-described first and second embodiments. Accordingly, an exercise motion status including an arm-swing angle can be suitably transmitted to the user, and exercise support for guiding the user to an appropriate exercise motion status can be performed.

In particular, in the present embodiment, exercise data obtained by the terminal worn on a human body can be transmitted as appropriate to the information communication device and the network server and stored in the memory section, and processing for providing evaluation information to the exercise data can be performed on the information communication device and the network server. Therefore, the terminal to be worn on a human body can be achieved with a device structure having a relatively small storage capacity (memory) and a simple arithmetic processing function.

In each of the above-described embodiments, the method is described in which evaluation information indicating whether or not the condition is desirable is provided to an obtained arm-swing angle in the arm-swing evaluation processing by the user US and a comparison with the current arm-swing angle is performed based on the arm-swing angle provided with the evaluation information in the arm-swing status judgment/support processing. However, the present invention is not limited thereto.

For example, in the arm-swing evaluation processing and the arm-swing status judgment/support processing, information regarding a footstep count and pitch calculated based on sensor data may be included as an element when evaluation information is provided and a comparison and judgment are made, in addition to the arm-swing angle.

Also, in each of the above-described embodiments, the terminals 100 and 200 constituting the exercise support device are worn on an upper arm portion and a forearm portion of a human body. Then, based on acceleration data detected by the terminals 100 and 200, a judgment is made as to the exercise motion status of the user (whether or not the user is running, walking, etc.), and one cycle (a period corresponding to one footstep) in the operation of detecting the arm-swing status (arm orientation) is set. However, the present invention is not limited thereto.

That is, in the present invention, a terminal having an acceleration sensor incorporated therein may be worn on the trunk of a human body such as a chest or hip portion to obtain the acceleration data described above.

By this structure, compared with the case where the terminal is worn on the upper arm portion or the forearm portion, a posture change does not occur very often, and acceleration near the gravity center of a human body during an exercise motion can be stably obtained. Therefore, an accurate acceleration not affected by arm swing can be detected, and a judgment as to an exercise motion status and setting of one cycle of the detecting operation can be suitably made.

While the present invention has been described with reference to the preferred embodiments, it is intended that the invention be not limited by any of the details of the description therein but includes all the embodiments which fall within the scope of the appended claims.

What is claimed is:

1. An exercise support device comprising:
   a detecting section which detects motion data related to a motion status of a user;
   a swing-angle obtaining section which obtains a swing angle of any of a plurality of parts which include an arm and a leg when the user is in a specific motion state with a swing motion of the any of the plurality of parts; and
   an information notifying section which notifies the user of exercise support information based on the swing angle obtained by the swing-angle obtaining section,
   wherein the swing-angle obtaining section obtains a maximum value of differences between angles of the any of the plurality of parts of the user at two different timings in one cycle of the swing motion as the swing angle, based on the motion data, and
   wherein the information notifying section includes at least one of a display section which displays visible information corresponding to the exercise support information, an acoustic section which emits sound information corresponding to the exercise support information, and a vibrating section which generates vibration information corresponding to the exercise support information.

2. The exercise support device according to claim 1, further comprising:
   a motion state judging section which judges whether or not the user is in the specific motion state, based on the motion data detected by the detecting section,
   wherein the swing-angle obtaining section obtains the swing angle, when the motion state judging section judges that the user is in the specific motion state.

3. The exercise support device according to claim 2, wherein the detecting section includes an acceleration sensor which detects acceleration occurring along with a motion of the user, and
   wherein the motion state judging section judges whether or not the user is in the specific motion state based on a value of the acceleration detected by the acceleration sensor.

4. The exercise support device according to claim 1, further comprising:
   an evaluation information storage section which stores evaluation information regarding the swing angle of the user such that the evaluation information corresponds to the swing angle; and
   a swing status judging section which judges whether or not the swing angle obtained by the swing-angle obtaining section is desirable based on a comparison between the swing angle obtained by the swing-angle obtaining section and the swing angle corresponding to the evaluation information stored in the evaluation information storage section,
   wherein the information notifying section notifies the user of the exercise support information for guiding the swing angle to a suitable angle based on a result of judgment by the swing status judging section.

5. The exercise support device according to claim 4, wherein the evaluation information storage section stores the evaluation information such that the evaluation information corresponds to the swing angle and circumstance information regarding the motion status of the user, and
   wherein the swing status judging section judges whether or not the swing angle obtained by the swing-angle obtaining section is desirable based on a comparison between the swing angle of the user obtained by the swing-angle obtaining section in a specific circumstance and the swing angle corresponding to the evaluation information of the user in the specific circumstance stored in the evaluation information storage section.

6. The exercise support device according to claim 4, wherein the detecting section is provided in a first terminal, and the information notifying section is provided in a second terminal that is different from the first terminal, and
   wherein the first terminal and the second terminal are wearable on different portions of the user to each other.

7. The exercise support device according to claim 4, wherein the detecting section and the information notifying section are provided in a single terminal.

8. The exercise support device according to claim 4, wherein the evaluation information storage section is connected to the detecting section and the information notifying section via a network.

9. The exercise support device according to claim 1, wherein the part is the arm of the user,
   wherein the detecting section includes an angular velocity sensor which detects angular velocity corresponding to a movement of the arm in the swing motion, and
   wherein the swing-angle obtaining section calculates angles of the arm in the swing motion based on a value obtained by integrating angular velocity data detected by the angular velocity sensor with respect to time; obtains angles of the arm at a plurality of timings when the angular velocity data in the one cycle has a minimum value; and obtains a maximum value of differences between angles of the arm at two different timings among the plurality of timings as the swing angle.

10. The exercise support device according to claim 9, wherein the detecting section further includes an acceleration sensor which detects acceleration occurring along with a motion of the user, and
wherein the swing-angle obtaining section detects landing timing of a foot of the user based on a change in a value of the acceleration detected by the acceleration sensor, and takes the landing timing as start timing and end timing of the one cycle when the swing angle is calculated.

11. The exercise support device according to claim 9, wherein the angular velocity sensor in the detecting section is wearable on the arm of the user.

12. The exercise support device according to claim 11, wherein the swing-angle obtaining section calculates, when the angular velocity sensor is being worn on the arm of the user, the swing angle based on the angular velocity data detected by the angular velocity sensor and a distance from a shoulder serving as a fulcrum of the arm where the angular velocity sensor is being worn to an area where the angular velocity sensor is being worn.

13. An exercise support method for an exercise support device including a detecting section which detects motion data related to a motion status of a user and an information notifying section which includes a display section, the exercise support method comprising:
a step of detecting, by the detecting section, motion data related to a motion status of a user;
a step of, when the user is in a specific motion state with a swing motion of any of a plurality of parts which include an arm and a leg, obtaining, for each one cycle of the swing motion, a maximum value of differences between angles of the any of the plurality of parts of the user at two different timings in each one cycle as a swing angle, based on the motion data; and
a step of displaying, on the display section, a swing angle obtained in one cycle before one cycle immediately before a present time.

14. The exercise support method according to claim 13, further comprising:
a step of judging whether or not the user is in the specific motion state based on the motion data,
wherein the swing angle is obtained when the user is judged to be in the specific motion state by the step of judging whether or not the user is in the specific motion state.

15. The exercise support method according to claim 13, further comprising:
a step of storing evaluation information regarding the obtained swing angle of the user in an evaluation information storage section such that the evaluation information corresponds to the swing angle;
a step of judging whether or not the obtained swing angle is desirable based on a comparison between the obtained swing angle and the swing angle corresponding to the evaluation information stored in the evaluation information storage section; and
a step of notifying the user of the exercise support information based on a result of the judgment.

16. The exercise support method according to claim 15, wherein the step of storing the evaluation information in the evaluation information storage section includes a step of storing the evaluation information in the evaluation information storage section such that the evaluation information corresponds to the swing angle and circumstance information regarding the motion status of the user, and
wherein the step of judging whether or not the swing angle is desirable includes a step of judging whether or not the swing angle is desirable based on a comparison between the obtained swing angle of the user in a specific circumstance and the swing angle corresponding to the evaluation information of the user in the specific circumstance stored in the evaluation information storage section.

17. The exercise support method according to claim 13, wherein the part is the arm of the user, and
wherein the step of obtaining the swing angle includes a step of calculating angles of the arm in the swing motion based on a value obtained by integrating, with respect to time, angular velocity data detected by an angular velocity sensor included in a detecting section which detects angular velocity corresponding to a motion of the arm in the swing motion; obtaining angles of the arm at a plurality of timings when the angular velocity data in the one cycle has a minimum value; and obtaining a maximum value of differences between angles of the arm at two different timings among the plurality of timings as a swing angle.

18. A non-transitory computer-readable storage medium having stored thereon an exercise support program that is executable by a computer of an exercise support device including a detecting section which detects motion data related to a motion status of a user and an information notifying section which includes a display section, the program being executable by the computer to perform functions comprising:
processing for detecting, by the detecting section, motion data related to a motion status of a user; and
processing for, when the user is in a specific motion state with a swing motion of any of a plurality of parts which include an arm and a leg, calculating, for each one cycle of the swing motion, a maximum value of differences between angles of the any of the plurality of parts of the user at two different timings in each one cycle as a swing angle, based on the motion data; and
processing for displaying, on the display section, a swing angle obtained in one cycle before one cycle immediately before a present time.

19. An exercise support device comprising:
a detecting section which detects motion data related to a motion status of a user,
a swing-angle obtaining section which obtains a swing angle of any of a plurality of parts which include an arm and a leg when the user is in a specific motion state with a swing motion of the any of the plurality of parts; and
an information notifying section which includes a display section which displays exercise motion information including the swing angle obtained by the swing-angle obtaining section,
wherein the swing-angle obtaining section obtains, for each one cycle of the swing motion, a maximum value of differences between angles of the any of the plurality of parts of the user at two different timings in each one cycle as a swing angle, based on the motion data, and
wherein the information notifying displays, on the display section, a swing angle obtained in one cycle before one cycle immediately before a present time.

* * * * *